United States Patent [19]

Shimotori et al.

[11] Patent Number: 4,792,565
[45] Date of Patent: Dec. 20, 1988

[54] PYRAZOLECARBONYLAMINE DERIVATIVES AND AGRICULTURAL AND HORTICULTURAL FUNGICIDES CONTAINING SAID COMPOUNDS

[75] Inventors: Hitoshi Shimotori; Tutomu Ishii; Hideo Yamazaki; Toshiaki Kuwatsuka, all of Yokohama; Yuji Yanase, Kamakura; Yoshinori Tanaka, Yokohama, all of Japan

[73] Assignee: Mitsui Toatsu Chemicals, Inc., Tokyo, Japan

[21] Appl. No.: 38,971

[22] Filed: Apr. 16, 1987

[30] Foreign Application Priority Data

Apr. 24, 1986 [JP] Japan ................. 61-93328
Jun. 18, 1986 [JP] Japan ................. 61-139981
Nov. 5, 1986 [JP] Japan ................. 61-262018

[51] Int. Cl.$^4$ ............... A01N 43/56; C07D 231/14; C07D 231/16; C07D 403/12
[52] U.S. Cl. ................. 514/406; 514/407; 548/374; 548/376; 548/377; 548/378
[58] Field of Search ............ 548/376, 377, 378, 374; 514/403, 404, 406, 407

[56] References Cited

U.S. PATENT DOCUMENTS 4,134,987 1/1979 Huppatz ................. 548/377
4,506,084 3/1985 Kay et al. ............... 549/492
4,515,959 5/1985 Kay et al. ............... 548/378

FOREIGN PATENT DOCUMENTS 0061836 10/1982 European Pat. Off. ......... 549/492
0076030 4/1983 European Pat. Off. ......... 548/374
0174088 3/1986 European Pat. Off. ......... 548/378
2701091 7/1977 Fed. Rep. of Germany ...... 548/377
167978 5/1982 Japan ..................... 514/403
122488 9/1984 Japan ..................... 514/403

OTHER PUBLICATIONS

*J. Chem. Soc.*, 1963, pp. 2143 to 2150.
*Synthesis*, 1972, No. 11, pp. 622 to 624.
*Bull. Soc. Chim. Fr.*, 1969, No. 11, pp. 4108 to 4111
*Justis Lieigs Ann Chem.*, 1972, 764, pp. 69 to 93.
*Aust. J. Chem.*, vol. 36, p. 135 (1983).
*Berichte der Deutschen Chemischen Gesellschaft*, vol. 59, p. 601 (1926).

*J. Chem. Soc.*, p. 3314, (1957).

*Primary Examiner*—Mary C. Lee
*Assistant Examiner*—Kurt G. Briscoe
*Attorney, Agent, or Firm*—Fisher, Christen & Sabol

[57] ABSTRACT

Novel pyrazole derivatives of the general formula (I)

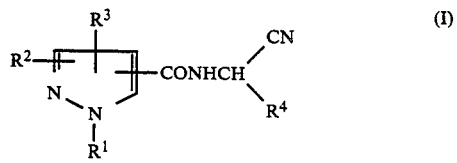

wherein $R^1$ represents an alkyl, haloalkyl, alkenyl, haloalkenyl or phenyl group, $R^2$ and $R^3$ each represent a hydrogen or halogen atom, or an alkyl, haloalkyl, alkoxy, alkoxyalkyl or phenyl group, and $R^4$ represents an alkyl, alkenyl, haloalkenyl or phenyl group, or a heterocyclic aromatic group which contains at least one of oxygen, nitrogen and sulfur atoms and may be unsubstituted or substituted, which are useful as agricultural and horticultural fungicides. The pyrazole derivatives can be produced by reacting compounds of the general formula (III)

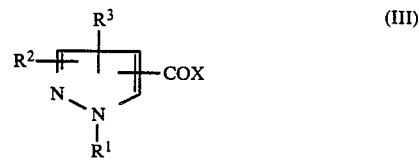

wherein $R^1$, $R^2$ and $R^3$ are as defined above, and X represents a halogen atom, with aminoacetonitriles of the general formula (IV)

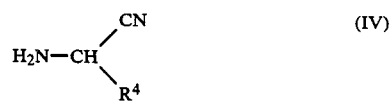

wherein $R^4$ is as defined above,
or salts thereof.

7 Claims, No Drawings

PYRAZOLECARBONYLAMINE DERIVATIVES AND AGRICULTURAL AND HORTICULTURAL FUNGICIDES CONTAINING SAID COMPOUNDS

This invention relates to pyrazole derivatives represented by the general formula (I)

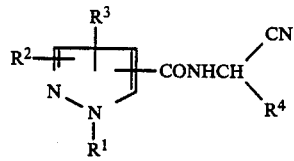

wherein $R^1$ represents an alkyl, haloalkyl, alkenyl, haloalkenyl or phenyl group, $R^2$ and $R^3$ each represent a hydrogen or halogen atom, or an alkyl, haloalkyl, alkoxy, alkoxyalkyl or phenyl group, and $R^4$ represents an alkyl, alkenyl, haloalkenyl or phenyl group, or a heterocyclic aromatic group which contains at least one of oxygen, nitrogen and sulfur atoms and may be unsubstituted or substituted.

The invention also pertains to a process for producing these pyrazole derivatives, and agricultural and horticultural fungicides containing them as active ingredients.

Much research has previously been undertaken on organic synthetic compounds useful in agriculture and horticulture, and a number of biologically active compounds have been found and come into practical use. Many active compounds of the amide series which are contained in the skeleton of the compounds of this invention have been found and some of them have been used as herbicides or fungicides. For example, as substituted benzamide derivatives, ethyl N-benzoyl-N-(3,4-dichlorophenyl-2-aminopropionate (benzoylpropethyl) useful as a herbicide and 2-methyl-N-(3-isopropoxyphenyl)benzamide (mepronil) useful as a fungicide are known. Herbicidally active compounds of the pyrazole series have also been known, and for example, 4-(2,4-dichlorobenzoyl)-1,3-dimethylpyrazol-5-yl p-toluenesulfonate (pyrazolate) and 4-(2,4-dichlorobenzoyl)-5-benzoylmethoxy-1,3-dimethylpyrazole (pyrazoxin) have been widely utilized in Japan as herbicides for paddies.

Japanese Laid-Open Patent Publication No. 167978/1982 discloses substituted acylaminoacetonitrile derivatives having a furan ring as herbicides and fungicides, but these compounds are phytotoxic to crops. This patent document discloses 4-pyridylcarbonyl, 2-furylcarbonyl, 2-thienylcarbonyl and 2-benzofurylcarbonyl groups as heterocyclic carbonyl groups which are acyl groups.

Chemical Abstracts describe some examples of synthesis of acylamino saturated aliphatic derivatives which are analogous to the pyrazole derivatives of the present invention. Specifically, examples of synthesis of 2-benzoylaminobutyronitrile are given in J. Chem. Soc., 1963, pages 2143-2150 and Synthesis, 1972, No. 11, pages 622-624, and examples of synthesis of 2-benzoylaminopropionitrile, in Bull. Soc. Chim. Fr., 1969, No. 11, pages 4108-4111 and Justus Liebigs Ann. Chem., 1972, 764, pages 69-93. These articles, however, are quite silent on the biological activities of the described compounds.

Synthetic compounds having various chemical structures have been used as agricultural and horticultural fungicides, and have played an unfathomably significant role in controlling plant diseases and consequently contributed to the development of agriculture. Some of these compounds, however, never have sufficient controlling activity and safety. For example, captafol, TPN, captan and dithiocarbamate chemicals have been widely used against late blight and powdery mildew of various cultivated plants and contributed to the increased production of crops. These compounds, however, mainly have a preventive effect against late blight and powdery milder, and cannot at all be expected to have a curative effect. Hence, they have the serious defect that they cannot be expected to produce a sufficient effect when applied after diseases have occurred. When actual control of plant diseases is considered, the chemicals should be applied more or less after diseases have occurred. Therefore, the plant diseases are difficult to control completely by these compounds. Furthermore, these compounds must be used in very high concentrations to exhibit a control effect, and their use is restricted for safety reasons. In addition, some of the above compounds have unnegligible toxicity to fish. To solve the above problems, extensive research has been continued on new controlling agents, and N-phenylalanine ester derivatives such as metalaxyl [methyl N-(2,6-dimethylphenyl)-N-(2'-methoxyacetyl)alaninate)] which show a superior preventive and curative effect have been developed as an agent for controlling plant diseases caused by Phycomycetes, and are gaining worldwide acceptance. The problem with these N-phenylalanine ester derivatives is that fungi acquiring resistance to these compounds have already appeared and their fungicidal effect is decreased.

It is an object of this invention to overcome the defects of the prior art described above, and to provide compounds having excellent properties as agricultural and horticultural fungicides, a process for production thereof, and agents for controlling noxious microorganisms comprising these compounds as active ingredients. More specifically, the object of this invention is to provide compounds which have both preventive and curative effects on crop diseases such as late blight and downy mildew, are widely applicable, and are not toxic to cultivated plants, warm-blooded animals and fish; a convenient process for production thereof in high yields; and useful agricultural compositions containing these compounds.

The present inventors have made extensive investigations on acylaminoacetonitrile derivatives, and found that a certain class of pyrazole derivatives have biological activity which cannot be anticipated from the compounds described hereinabove and have an excellent control effect against a wide range of plant diseases as agricultural and horticultural fungicides, and particularly, excellent preventive and curative control effects against crop diseases, such as late blight and downy mildew.

Thus, according to this invention, there are provided novel pyrazole derivatives represented by the general formula (I)

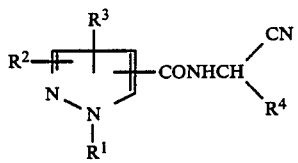 (I)

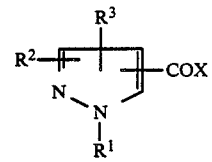 (III)

wherein $R^1$ represents an alkyl, haloalkyl, alkenyl, haloalkenyl or phenyl group, $R^2$ and $R^3$ each represent a hydrogen or halogen atom, or an alkyl, haloalkyl, alkoxy, alkoxyalkyl or phenyl group, and $R^4$ represents an alkyl, alkenyl, haloalkenyl or phenyl group, or a heterocyclic aromatic group which contains at least one of oxygen, nitrogen and sulfur atoms and may be unsubstituted or substituted.

In general formula (I), $R^1$ represents an alkyl group, preferably an alkyl group having 1 to 12 carbon atoms, more preferably a lower alkyl group having 1 to 6 carbon atoms, a haloalkyl group, preferably a lower haloalkyl group having 1 to 6 carbon atoms, an alkenyl group, preferably a lower alkenyl group having 2 to 6 carbon atoms, a haloalkenyl group, preferably a lower haloalkenyl group havin 2 to 6 carbon atoms, or a phenyl group. Each of $R^2$ and $R^3$ represents a hydrogen atom, a halogen atom, an alkyl group, preferably a lower alkyl group having 1 to 6 carbon atoms, a haloalkyl group, preferably a lower haloalkyl group having 1 to 6 carbon atoms, an alkoxy group, preferably a lower alkoxy group having 1 to 6 carbon atoms, an alkoxyalkyl group, preferably a lower alkoxyalkyl group having 2 to 6 carbon atoms, or a phenyl group. $R^4$ represents an alkyl group, preferably a lower alkyl group having 1 to 6 carbon atoms, an alkenyl group, preferably an alkenyl group having 2 to 12 carbon atoms, more preferably a lower alkenyl group having 2 to 6 carbon atoms, a haloalkenyl group, preferably a lower haloalkenyl group having 2 to 6 carbon atoms, a phenyl group, or a heterocyclic aromatic group which contains at least one of oxygen, nitrogen and sulfur atoms and which is unsubstituted or substituted, preferably a furyl, thienyl or pyrrole group.

Furthermore, the present inventors have extensively studied a process for producing the pyrazole derivatives of general formula (I), and found a process which gives the desired products in high yield.

Thus, according to this invention, there is provided a process for producing pyrazole derivative of general formula (I), which comprises reacting compounds represented by the general formula (III)

wherein $R^1$, $R^2$ and $R^3$ are as defined above, and X represents a halogen atom, with aminoacetonitriles of the general formula (IV)

 (IV)

wherein $R^4$ is as defined above,
or salts thereof.

Most of the pyrazole carboxylic acid chlorides (III) used as a starting material in the process of this invention can be easily produced through the routes shown in reactions (A) to (E) below in accordance with, for example, the methods described in Aust. J. Chem., vol. 36, page 135 (1983), and Berichte der Deutschen Chemischen Gesellschaft, vol. 59, page 601 (1926).

Reaction (A)

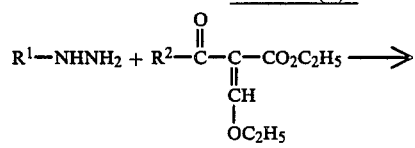

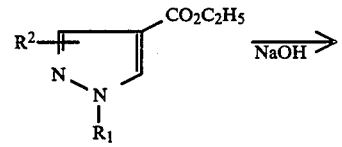

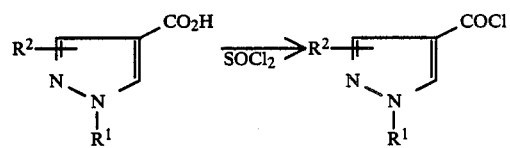

Where $R^2$ or $R^3$ is a methoxy group, the compounds of formula (III) can be synthesized by the route hown by reaction (B) below in accordance with the method isclosed in Japanese Laid-Open Patent Publication No. 122488/1984.

Reaction (B)

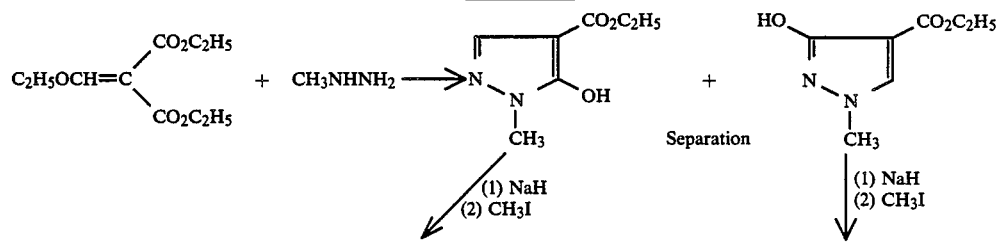

-continued
Reaction (B)

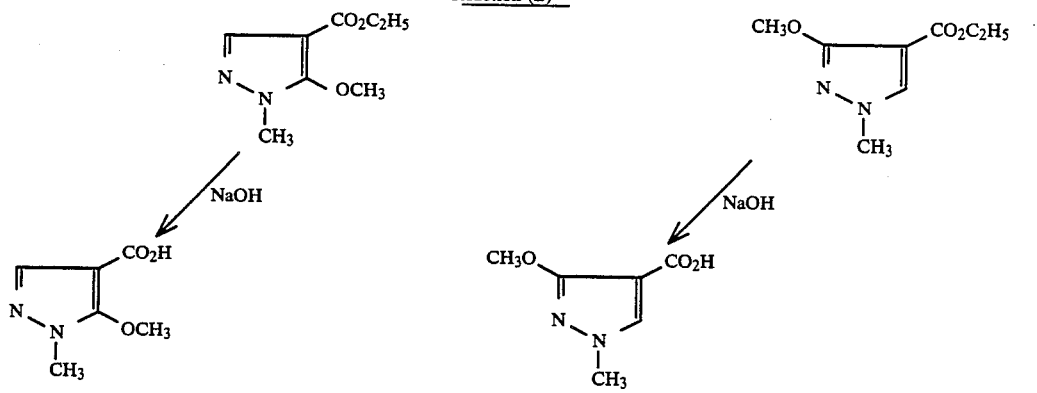

Furthermore, as shown in reaction (C) below, a substituent may be introduced later into the nitrogen atom of the pyrazole ring by using $R^1X$ ($R^1$ and X are as defined above).

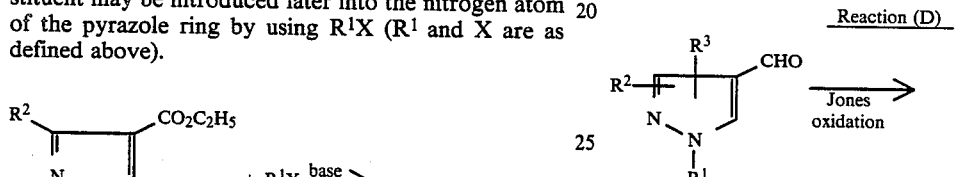

Reaction (D)

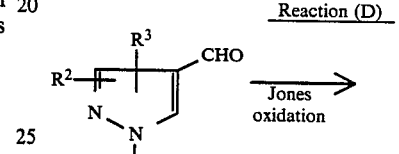

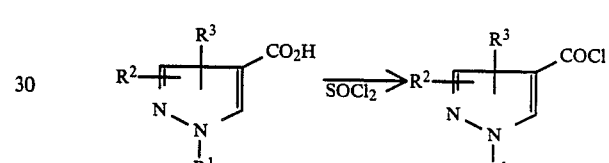

Pyrazole-5-carboxylic acids may be obtained by the method shown in reaction (E).

Reaction (E)

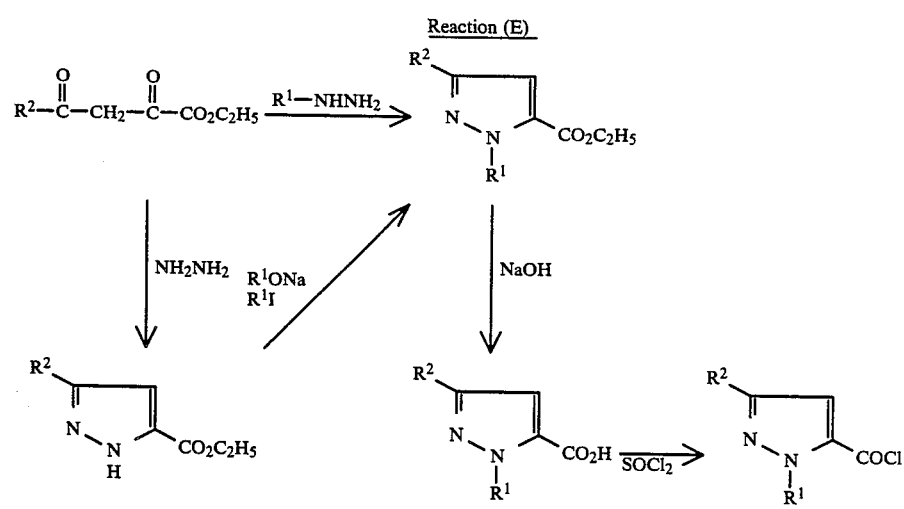

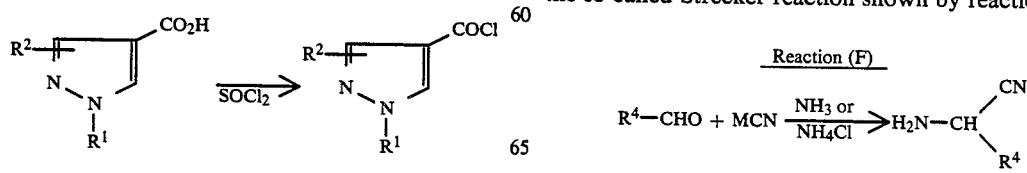

Pyrazole carboxylic acids may be obtained by oxidizing pyrazolealdehydes by reaction (D).

The aminoacetonitriles (IV) can be easily obtained by the so-called Strecker reaction shown by reaction (F).

Reaction (F)

$$R^4-CHO + MCN \xrightarrow[NH_4Cl]{NH_3 \text{ or}} H_2N-CH\begin{smallmatrix}CN\\R^4\end{smallmatrix}$$

(V)    (VI)         (IV)

Specifically, they can be easily obtained by reacting aldehydes of general formula (V) with hydrogen cyanide (VI, M=H) or an alkali metal cyanide (VI, M=alkali metal) and ammonia or ammonium chloride in water or a two layer system of water and an organic solvent. The sequence of adding the aldehyde (V), the cyanide (VI) and ammonia or ammonium chloride is optional. In many cases, the addition of a phase transfer catalyst makes the reaction proceed more efficiently. Since the resulting aminoacetonitriles are unstable, it is desirable to submit them immediately to the next step. However, mineral acid salts of the aminoacetonitriles are stable solids and can be stored for a long period of time.

The process for producing the compounds of general formula (I) in accordance with this invention will be described with reference to reaction (G).

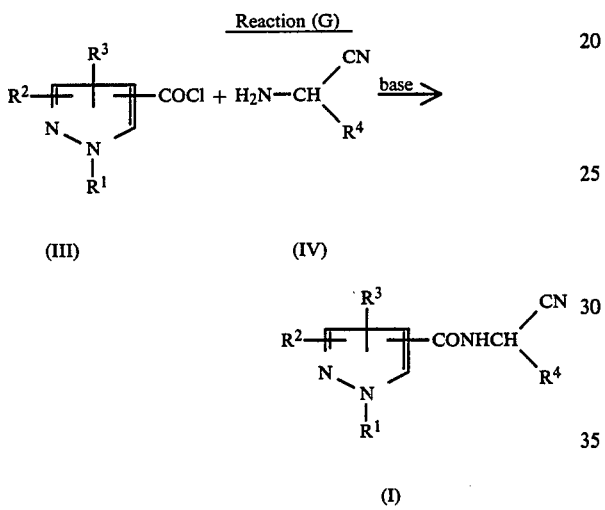

Reaction (G)

(III)  (IV)

(I)

The aminoacetonitrile (IV) is dissolved in a solvent inert to the present reaction, and an equivalent, or a slightly excess, of a base is added. Then, the pyrazolecarboxylic acid chloride (III) is gradually added dropwise. When the aminoacetonitrile salt is used, a base required to neutralize it is additionally supplied. Examples of the inert solvent include ethers such as diethyl ether, diisopropyl ether, tetrahydrofuran and dioxane; hydrocarbons such as benzene, toluene, xylene and ligroin; halogenated hydrocarbons such as dichloromethane, chloroform and carbon tetrachloride; esters such as ethyl acetate and ethyl propionate; and aprotic polar solvents such as N,N-dimethylformamide, dimethyl sulfoxide and 1,3-dimethylimidazolidinone. Pyridine can be used both as the base and the solvent. Examples of the base are organic bases such as triethylamine, dimethylaniline and pyridine, and inorganic bases such as ammonia, potassium carbonate, sodium carbonate, sodium hydrogen carbonate, sodium hydroxide and ammonium carbonate. This reaction should not be carried out at too high a temperature since the thermal stability of the alpha-aminoacetonitrile derivative (IV) is low. Furthermore, since this is an exothermic reaction, it is desirably carried out under cooling (0° to 5° C.). After the addition, the mixture is stirred at room temperature to complete the reaction. The reaction time which may vary depending upon the reaction temperature is usually 0.5 to 4 hours. After the reaction, the crude product is obtained in a customary manner. The resulting pyrazole derivative can be easily isolated and purified by conventional methods such as recrystallization and column chromatography.

The present invention further provides an agricultural and horticultural fungicide comprising a pyrazole derivative of general formula (I) as an active ingredient. As an agricultural and horticultural fungicide, the compounds of this invention show a control effect on a wide range of plant diseases, especially late blight and downy mildew of various crops caused by Phycomycetes. Main plant diseases that can be controlled by the compounds of this invention include potato late blight (*Phytophthora infestans*), tomato late blight (*Phytophthora infestans*), tabaco black shank (*Phytophthora parasitica* var. *nicotiana*), strawberry leather rot (*Phytophthora cactorum*), downy mildew of garland chrysanthemum (*Peronospora chrysanthemi*), Phytophthora rot of adzuki bean, vine downy mildew (*Plasmopara viticola*), cucumber downy mildew (*Pseudoperonospora cubensis*), hop downy mildew (*Pseudoperonospora humuli*), and seedling damping off of various crops caused by fungi of the genera Pythium and Aphanomyces.

The compounds of this invention may be applied by seed dressing, foliar application, soil treatment, etc. They exhibit a sufficient efficacy by using any of the methods usually employed by those skilled in the art. The rate of application and the concentration of the chemical to be applied may vary depending upon the crop to be protected, the disease to be controlled, the degree of occurrence of the disease, the formulation of the chemical, the method of application and various environmental conditions. The rate of application by spraying is suitably 5 to 200 g, preferably 10 to 100 g, per are. The suitable spray concentration is 10 to 500 ppm, preferably 50 to 300 ppm.

The agricultural and horticultural fungicide of this invention may be used together with agricultural chemicals such as other fungicides, insecticides, herbicides or plant growth regulating agents, soil conditioners and fertilizers. They may be prepared into mixed formulations prior to use.

The compounds of this invention may be applied directly, but preferably in the form of a composition comprising a solid or liquid carrier including a solid or liquid diluent. The carrier, as referred to herein, denotes a synthetic or natural inorganic or organic substance which is incorporated in order to aid in arrival of the active ingredients at a site to be treated or to facilitate storage, transportation and handling of the active ingredients.

Suitable solid carriers include, for example, clays such as montmorillonite and kaolinite, inorganic substances such as diatomaceous earth, terra abla, talc, vermiculite, gypsum, calcium carbonate, silica gel and ammonium sulfate, vegetable organic substances such as soybean meal, sawdust and wheat flour, and urea.

Suitable liquid carriers include, for example, aromatic hydrocarbons such as toluene, xylene and cumene, paraffinic hydrocarbons such as kerosene and mineral oils, halogenated hydrocarbons such as carbon tetrachloride, chloroform and dichloroethane, ketones such as acetone and methyl ethyl ketone, ethers such as dioxane and tetrahydrofuran, alcohols such as methanol, propanol and ethylene glycol, dimethylformamide, dimethyl sulfoxide, and water.

Various adjuvants may be used singly or in combination depending upon the type of the formulation, the situation of application, etc. in order to enhance the efficacy of the compounds of this invention further. For example, anionic surface-active agents (such as ligninsulfonic acid salts, alkylbenzenesulfonic acid salts and alkylsulfate esters), nonionic surface-active agents (such as polyoxyalkylene alkyl ethers, polyoxy alkylene alkylaryl ethers, polyoxyalkylene alkylamines, polyoxyalkylene alkylamides, polyoxyalkylene alkylthio ethers, polyoxyalkylene fatty acid esters, glycerol fatty acid esters, sorbitan fatty acid esters, polyoxyalkylene sorbitane fatty acid esters and polyoxypropylene polyoxyethylene block polymers), lubricants (such as calcium stearate and waxes), stabilizers (such as isopropyl hydrogen phosphate), methyl cellulose, carboxymethyl cellulose, casein, and gum arabic may be used for the purpose of emulsification, dispersion, spreading, wetting, binding, stabilization, etc.

The amount of the active ingredient in the composition of the compound of this invention is usually 0.5 to 20% by weight for a dust, 5 to 20% by weight for an emulsifiable concentrate, 10 to 90% by weight for a wettable powder, 0.1 to 20% by weight for granules, and 10 to 90% by weight for a flowable agent. On the other hand, the amount of the carrier in the formulation is usually 60 to 99% by weight for the dust, 60 to 95% by weight for the emulsifiable concentrate, 10 to 90% by weight for the wettable powder, 80 to 99% by weight for the granules, and 10 to 90% by weight for the flowable agent. The amount of adjuvants is usually 0.1 to 20% by weight for the dust, 1 to 20% by weight for the emulsifiable concentrate, 0.1 to 20% by weight for the wettable powder, 0.1 to 20% by weight for the granules, and 0.1 to 20% by weight for the flowable agent.

Typical examples of the pyrazole derivatives of this invention represented by general formula (I) are shown in Table 1.

TABLE 1

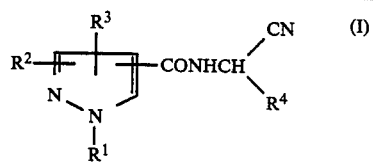

| Compound No. | $R^1$ | $R^2$ | $R^3$ | $R^4$ | Physical property (m.p. °C.) | NMR (100MHz) |
|---|---|---|---|---|---|---|
| 1 | $CH_3-$ | 3-$CH_3$ | 5-H | $-CH=C\begin{smallmatrix}CH_3\\CH_3\end{smallmatrix}$ | 110.5~111.5 | $\delta_{TMS}^{CDCl_3}$ (ppm): 1.78(6H, s), 2.46(3H, s), 3.82(3H, s), 5.31(1H, d, J=8.0Hz), 5.68(1H, dd, J=8.0Hz, J=8.0Hz), 6.78(1H, d, J=8.0Hz), 7.81(1H, s) |
| 2 | $C_2H_5-$ | 3-$CH_3$ | 5-H | $-CH=C\begin{smallmatrix}CH_3\\CH_3\end{smallmatrix}$ | 115~116 | $\delta_{TMS}^{CDCl_3}$ (ppm): 1.45(3H, t, J=7.0Hz), 1.79(6H, s), 2.45(3H, s), 4.09(2H, s), 4.09(2H, q, J=7.0Hz), 5.29(1H, d, J=8.0Hz), 5.69(1H, dd, J=8.0Hz, J=8.0Hz), 6.81(1H, d, J=8.0Hz), 7.84(1H, s) |
| 3 | $CH_3\text{\textbackslash}CH-\text{/}CH_3$ | 3-$CH_3$ | 5-H | $-CH=C\begin{smallmatrix}CH_3\\CH_3\end{smallmatrix}$ | 95~96 | $\delta_{TMS}^{CDCl_3}$ (ppm): 1.45(6H, d, J=7.0Hz), 1.77(6H, s), 2.46(3H, s), 4.40(1H, m, J=7.0Hz), 5.3(1H, d, J=8.0Hz), 5.70(1H, dd, J=8.0Hz, J=8.0Hz), 6.70(1H, d, J=8.0Hz), 7.86(1H, s) |
| 4 | $CH_3-$ | 3-$CH_3$ | 5-H | $-CH=C\begin{smallmatrix}Cl\\CH_3\end{smallmatrix}$ | 113~114 | $\delta_{TMS}^{CDCl_3}$ (ppm): 2.19(3H, s), 2.47(3H, s), 3.80(3H, s), 5.60-5.82(2H, m), 6.79-7.02(1H, m), 7.75(1H, s) |
| 5 | $CH_3-$ | 3-$CH_3$ | 5-H | $-CH=CH.CH_3$ | 109~110 | $\delta_{TMS}^{CDCl_3}$ (ppm): 1.75(3H, d, J=7.0Hz), 2.46(3H, s), 3.84(3H, s), 5.4-6.3(3H, m), 6.68-6.80(1H, br s), 7.83(1H, s) |

TABLE 1-continued

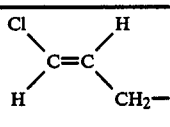

(I)

| Compound No. | R¹ | R² | R³ | R⁴ | Physical property (m.p. °C.) | NMR (100MHz) |
|---|---|---|---|---|---|---|
| 6 | 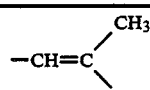 (Z) | 3-CH₃ | 5-H | $-CH=C\begin{matrix}CH_3\\CH_3\end{matrix}$ | Oil | $\delta^{CDCl_3}_{TMS}$ (ppm): 1.81(6H, s), 2.48(3H, s), 4.61(2H, d, J=6.0Hz), 5.25(1H, br), 5.61(1H, dd, J=7.0 & 10.0Hz), 5.9–6.2(2H, m), 6.65(1H, d, J=7.0Hz), 7.78(1H, s) |
| 7 | 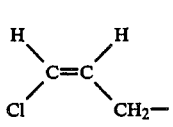 (E) | 3-CH₃— | 5-H | $-CH=C\begin{matrix}CH_3\\CH_3\end{matrix}$ | Oil | $\delta^{CDCl_3}_{TMS}$ (ppm): 1.81(6H, s), 2.47(3H, s), 4.80(2H, dd, J=6.0 & 1.0Hz), 5.26(1H, br), 5.63(1H, dd, J=7.0 & 10.0Hz), 5.9–6.3(2H, m), 6.73(1H, d, J=7.0Hz), 7.80(1H, s) |
| 8 | 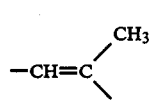 | 3-CH₃— | 5-H | $-CH=C\begin{matrix}CH_3\\CH_3\end{matrix}$ | 103~104.5 | $\delta^{CDCl_3}_{TMS}$ (ppm): 1.76(6H, s), 2.50(3H, s), 5.32(1H, br), 5.68(1H, br), 6.81(1H, br), 7.2–7.7(5H, m), 8.24(1H, s) |
| 9 | CH₃— | 3-H | 5-H | $-CH=C\begin{matrix}CH_3\\CH_3\end{matrix}$ | 133~135 | $\delta^{CDCl_3}_{TMS}$ (ppm): 1.77(6H, s), 3.89(3H, s), 5.30(1H, br), 5.68(1H, br), 7.52(1H, d, J=7.5Hz), 7.84(1H, s), 7.92(1H, s) |
| 10 | CH₃ |  | 5-H | $-CH=C\begin{matrix}CH_3\\CH_3\end{matrix}$ | 146~147.5 | $\delta^{DMSO-d_6}_{TMS}$ (ppm): 1.70(3H, s), 1.77(3H, s), 3.66(3H, s), 5.20–5.52(2H, m), 7.45(5H, d), 7.96(1H, s), 8.62(1H, d, J=7.0Hz) |
| 11 | CH₃— | 3-H | 5-H | 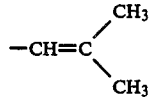 | 128~129.5 | $\delta^{DMSO-d_6}_{TMS}$ (ppm): 1.72(3H, s), 1.76(3H, s), 3.87(3H, s), 5.28–5.60(2H, m), 7.30–7.42(3H, m), 8.16(1H, s), 8.72(1H, d, J=7.0Hz) |
| 12 | CH₃— | 3-CH₃ | 5-Cl | $CH=C\begin{matrix}CH_3\\CH_3\end{matrix}$ | 140~141 | $\delta^{DMSO-d_6}_{TMS}$ (ppm): 1.76(3H, s), 1.77(3H, s), 2.27(3H, s), 3.74(3H, s), 5.2–5.6(2H, m), 8.48(1H, d, J=7.0Hz) |
| 13 | CH₃CH₂CH₂CH₂— | 3-H | 5-H | $-CH=C\begin{matrix}CH_3\\CH_3\end{matrix}$ | Oil | $\delta^{CDCl_3}_{TMS}$ (ppm): 0.92(3H, t, J=7.0Hz), 1.1–1.5(2H, m), 1.7–1.9(8H, m), 4.15(2H, t, J=7.0Hz), 5.34(1H, d, J=7.0Hz), 5.73(1H, dd, J=7.0 & 7.0Hz), 7.68(1H, d, J=7.0Hz), 7.92(1H, s), 7.99(1H, s) |
| 14 | CH₂=CH—CH₂— | 3-CH₃ | 5-H | $-CH=C\begin{matrix}CH_3\\CH_3\end{matrix}$ | Oil | $\delta^{CDCl_3}_{TMS}$ (ppm): 1.81(6H, s), 2.49(3H, s), 4.48–4.78(2H, m), 4.98–5.40(3H, m), 5.52–6.20(2H, m), 7.09(1H, d, J=8.0Hz), 7.86(1H, s) |

TABLE 1-continued $$\text{(I)} \quad R^2 \underset{\underset{R^1}{N}}{\overset{R^3}{\underset{N}{\bigcirc}}} \text{—CONHCH} \underset{R^4}{\overset{CN}{\diagdown}}$$

| Compound No. | In general formula (I) R¹ | R² | R³ | R⁴ | Physical property (m.p. °C.) | NMR (100MHz) |
|---|---|---|---|---|---|---|
| 15 | CH₃— | 3-CF₃ | 5-H | —CH=C(CH₃)CH₃ | 114~115 | $\delta^{CDCl_3}_{TMS}$ (ppm): 1.87(6H, s), 3.95(3H, s), 5.19-5.38(1H, m), 5.55(1H, dd, J=8.0 & 8.0Hz), 6.74(1H, d, J=8.0Hz), 7.97(1H, s) |
| 16 | C₂H₅— | 3-H | 5-CH₃ | —CH=C(CH₃)CH₃ | Oil | $\delta^{CDCl_3}_{TMS}$ (ppm): 1.37(3H, t, J=7.0Hz), 1.76(6H, s), 2.56(3H, s), 4.09(2H, q, J=7.0Hz), 5.20-5.40(1H, m), 5.69(1H, dd, J=8.0 & 8.0Hz), 7.79(1H, d, J=8.0Hz), 7.84(1H, s) |
| 17 | CH₃— | 3-CH₃ | 5-CH₃ | —CH=C(CH₃)CH₃ | 148~149 | $\delta^{DMSO-d_6}_{TMS}$ (ppm): 1.77(3H, s), 1.78(3H, s), 2.23(3H, s), 2.33(3H, s), 3.66(3H, s), 5.28-5.62(2H, m), 8.10-8.24(1H, m) |
| 18 | CH₃CH₂CH₂— | 3-CH₃ | 5-H | —CH=C(CH₃)CH₃ | Oil | $\delta^{CDCl_3}_{TMS}$ (ppm): 0.94(3H, t, J=6.0Hz), 1.76(6H, s), 1.88(2H, m), 2.48(3H, s), 4.08(2H, m), 5.30(1H, m), 5.72(1H, t, J=8.0Hz), 6.72(1H, d, J=8.0Hz), 7.84(1H, s) |
| 19 | CH₃CH₂CH₂CH₂— | 3-CH₃ | 5-H | —CH=C(CH₃)CH₃ | Oil | $\delta^{CDCl_3}_{TMS}$ (ppm): 0.90(3H, t, J=6.0Hz), 1.24(2H, m), 1.5-2.0(8H, m), 2.44(3H, s), 4.00(2H, t, J=6.0Hz), 5.24(1H, m), 5.64(1H, t, J=8.0Hz), 6.74(1H, d, J=8.0Hz), 7.76(1H, s) |
| 20 | (CH₃)₂CHCH₂— | 3-CH₃ | 5-H | —CH=C(CH₃)CH₃ | Oil | $\delta^{CDCl_3}_{TMS}$ (ppm): 0.86(3H, d, J=2.0Hz), 0.94(3H, d, J=2.0Hz), 1.78(6H, s), 2.48(3H, s), 3.84(3H, m), 5.36(1H, m), 5.72(1H, t, J=8.0Hz), 6.88(1H, t, J=8.0Hz), 7.82(1H, s) |
| 21 | (CH₃)₃C— | 3-CH₃ | 5-H | —CH=C(CH₃)CH₃ | 117~120 | $\delta^{DMSO-d_6}_{TMS}$ (ppm): 1.60(9H, s), 1.74(3H, s), 1.78(3H, s), 2.70(3H, s), 5.50(2H, m), 7.84(1H, s), 8.72(1H, d, J=8.0Hz) |
| 22 | CH₃(CH₂)₄CH₂— | 3-CH₃ | 5-H | —CH=C(CH₃)CH₃ | Oil | $\delta^{DMSO-d_6}_{TMS}$ (ppm): 0.88(3H, t, J=6.0Hz), 1.1-1.5(8H, m), 1.76(3H, s), 1.80(3H, s), 2.36(3H, s), 4.04(2H, t, J=6.0Hz), 5.50(2H, m), 8.16(1H, s), 8.60(1H, d, J=8.0Hz) |

TABLE 1-continued $$\text{(I)}$$

Structure: R²-C(R³)=C-CONHCH(CN)(R⁴) in pyrazole ring with N-N-R¹

| Compound No. | R¹ | R² | R³ | R⁴ | Physical property (m.p. °C.) | NMR (100MHz) |
|---|---|---|---|---|---|---|
| 23 | CH₃(CH₂)₆CH₂— | 3-CH₃ | 5-H | —CH=C(CH₃)(CH₃) | Oil | $\delta^{CDCl_3}_{TMS}$ (ppm): 0.96(3H, t, J=6.0Hz), 1.05–1.5(10H, m), 1.84(8H, s), 2.36(3H, s), 4.00(2H, m), 5.26(1H, m), 5.64(1H, t, J=8.0Hz), 6.70(1H, d, J=8.0Hz), 7.80(1H, s) |
| 24 | CH₃— | 3-C₂H₅ | 5-H | —CH=C(CH₃)(CH₃) | Oil | $\delta^{DMSO-d_6}_{TMS}$ (ppm): 1.16(3H, t, J=8.0Hz), 1.74(3H, s), 1.78(3H, s), 2.80(2H, q, J=8.0Hz), 3.80(3H, s), 5.50(2H, m), 8.10(1H, s), 8.62(1H, d, J=8.0Hz) |
| 25 | CH₃— | 3-CH₂CH₂CH₃ | 5-H | —CH=C(CH₃)(CH₃) | 92~95 | $\delta^{DMSO-d_6}_{TMS}$ (ppm): 0.90(3H, t, J=8.0Hz), 1.60(2H, m, J=8.0Hz), 1.74(3H, s), 1.78(3H, s), 2.76(2H, t, J=8.0Hz), 3.80(3H, s), 5.48(2H, m), 8.12(1H, s), 8.64(1H, d, J=8.0Hz) |
| 26 | CH₃— | 3-CH(CH₃)(CH₃) | 5-H | —CH=C(CH₃)(CH₃) | 99~101 | $\delta^{DMSO-d_6}_{TMS}$ (ppm): 0.98(6H, d, J=6.0Hz), 1.72(3H, s), 1.76(3H, s), 3.40(1H, m), 3.76(3H, s), 5.40(2H, m), 8.00(1H, s), 8.50(2H, d, J=6.0Hz) |
| 27 | CH₃— | 3-CH₂CH₂CH₂CH₃ | 5-H | —CH=C(CH₃)(CH₃) | Oil | $\delta^{DMSO-d_6}_{TMS}$ (ppm): 0.90(3H, t, J=6.0hz), 1.40(4H, m), 1.76(3H, s), 1.78(3H, s), 2.80(2H, m), 3.80(3H, s), 5.50(2H, m), 8.10(1H, s), 8.60(1H, d, J=8.0Hz) |
| 28 | CH₃CH₂CH₂CH₂— | 3-C₂H₅ | 5-H | —CH=C(CH₃)(CH₃) | Oil | $\delta^{CDCl_3}_{TMS}$ ppm: 0.92(2H, m), 1.26(6H, t, J=8.0Hz), 1.6–2.0(8H, m), 2.90(2H, q, J=8.0Hz), 4.00(2H, m), 5.28(1H, m), 5.68(1H, t, J=8.0Hz), 6.76(1H, d, J=8.0Hz), 7.76(1H, s) |
| 29 | (CH₃)₃C— | 3-C₂H₅ | 5-H | —CH=C(CH₃)(CH₃) | Oil | $\delta^{DMSO-d_6}_{TMS}$ (ppm): 1.24(3H, t, J=8.0Hz), 1.68(9H, s), 1.82(3H, s), 1.86(3H, s), 3.18(2H, t, J=8.0Hz), 5.50(2H, m), 7.82(1H, s), 8.64(1H, d, J=8.0Hz) |
| 30 | CH₃ | 3-CH₃ | 5-H | 2-thienyl | 129~130 | $\delta^{CDCl_3}_{TMS}$ (ppm): 2.43(3H, s), 3.80(3H, s), 6.43(1H, d, J=8.0Hz), 7.0–7.58(4H, m), 7.79(1H, s) |

TABLE 1-continued $$\begin{array}{c} R^2 \underset{N}{\overset{R^3}{\underset{|}{\bigsqcup}}} \text{CONHCH} \overset{CN}{\underset{R^4}{\diagdown}} \end{array} \quad (I)$$

| Compound No. | R¹ | R², In general formula (I) R³ | R⁴ | Physical property (m.p. °C.) | NMR (100MHz) |
|---|---|---|---|---|---|---|
| 31 | C₂H₅ | 3-CH₃ | 5-H | 2-thienyl (methyl) | 99~100 | δ$_{TMS}^{CDCl_3}$ (ppm): 1.45(3H, t, J=7.0Hz), 2.46(3H, s), 4.095(2H, q, J=7.0Hz), 6.45(1H, d, J=8.0Hz), 6.78(1H, d, J=8.0Hz), 6.95-7.42(3H, m), 7.82(1H, s) |
| 32 | (CH₃)₂CH— | 3-CH₃ | 5-H | 2-thienyl | 140.5~141.5 | δ$_{TMS}^{CDCl_3}$ (ppm): 1.43(6H, d, J=7.0Hz), 2.43(3H, s), 4.36(1H, m, J=7.0Hz), 6.43(1H, d, J=7.0Hz), 6.95-7.40(4H, m), 7.88(1H, s) |
| 33 | CH₃— | 3-CH₃ | 5-H | 2-furyl | 121.5~122.5 | δ$_{TMS}^{CDCl_3}$ (ppm): 2.39(3H, s), 3.74(3H, s), 6.24(1H, d, J=8.0Hz), 6.28-6.52(2H, m), 7.36(1H, br s), 7.53(1H, d, J=8.0Hz), 7.83(1H, s) |
| 34 | C₂H₅— | 3-CH₃ | 5-H | 2-furyl | Semisolid | δ$_{TMS}^{CDCl_3}$ (ppm): 1.42(3H, t, J=7.0Hz), 2.43(3H, s), 4.015(2H, q, J=7.0Hz), 6.27(1H, d, J=8.0Hz), 6.28-6.30(2H, m), 7.02(1H, d, J=8.0Hz), 7.35(1H, br s), 7.77(1H, s) |
| 35 | (CH₃)₂CH— | 3-CH₃ | 5-H | 2-thienyl | Semisolid | δ$_{TMS}^{CDCl_3}$ (ppm): 1.46(6H, d, J=7.0Hz), 2.43(3H, s), 4.41(1H, m, J=7.0Hz), 6.38(1H, d, J=8.0Hz), 6.40-6.60(2H, m), 6.87(1H, d, J=8.0Hz), 7.45(1H, br s), 7.88(1H, s) |
| 36 | CH₃— | 3-CH₃ | 5-H | 3-methyl-2-thienyl | 167.5~168.5 | δ$_{TMS}^{CDCl_3}$ (ppm): 2.28(3H, s), 2.35(3H, s), 3.78(3H, s), 6.42(1H, d, J=8.0Hz), 6.88(1H, d, J=5.0Hz), 7.39(1H, d, J=5.0Hz), 8.17(1H, s), 9.02(1H, d, J=8.0Hz) |
| 37 | CH₃— | 3-CH₃ | 5-H | 5-bromo-2-thienyl | 132.5~133 | δ$_{TMS}^{CDCl_3}$ (ppm): 2.42(3H, s), 3.80(3H, s), 6.31(1H, d, J=9.0Hz), 6.9-7.4(3H, m), 7.76(1H, s) |
| 38 | CH₃— | 3-CH₃ | 5-H | 3-thienyl | 113~114.5 | δ$_{TMS}^{CDCl_3}$ (ppm): 2.42(3H, s), 3.79(3H, s), 6.42(1H, d, J=8.5Hz), 7.11(1H, dd, J=5.0 & 2.0Hz), 7.28-7.45(2H, m), 7.76(1H, s) |

TABLE 1-continued

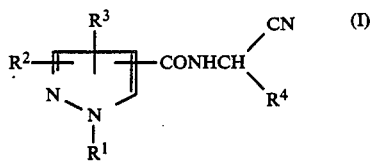

| Compound No. | R¹ | R² | R³ | R⁴ | Physical property (m.p. °C.) | NMR (100MHz) |
|---|---|---|---|---|---|---|
| 39 | CH₃— | 3-CH₃ | 5-H | ![2-methyl-5-methylthienyl] | 140.5~142.5 | $\delta^{CDCl_3}_{TMS}$ (ppm): 2.45(3H, s), 2.47(3H, s), 3.78(3H, s), 6.25(1H, d, J=8.0Hz), 6.58(1H, d, J=4.0Hz), 6.96(1H, d, J=4.0Hz), 7.10(1H, d, J=8.0Hz), 7.75(1H, s) |
| 40 | C₆H₅— | 3-CH₃ | 5-H | 2-methylthienyl | 154~155.5 | $\delta^{CDCl_3}_{TMS}$ (ppm): 2.51(3H, s), 6.42(1H, d, J=8.0Hz), 6.9-7.0(1H, m), 7.1-7.6(9H, m), 8.27(1H, s) |
| 41 | CH₃— | 3-CH₃ | 5-Cl | 2-methylthienyl | 159~161 | $\delta^{DMSO-d_6}_{TMS}$ (ppm): 2.36(3H, s), 3.81(3H, s), 6.54(1H, d, J=8.0Hz), 7.00-7.16(1H, m), 7.26-7.36(1H, m), 7.58-7.64(1H, m), 9.12(1H, d, J=8.0Hz) |
| 42 | CH₃— | 3-CH₃ | 5-H | 2-methyl-1H-pyrrolyl | 174~176 | $\delta^{CDCl_3}_{TMS}$ (ppm): 2.14(3H, s), 3.77(3H, s), 6.0-6.3(3H, m), 6.74-6.84(1H, m), 8.18(1H, s), 8.84(1H, d, J=8.0Hz) |
| 43 | CH₃— | 3-CH₃ | 5-H | 2-methylfuryl | 105~107 | $\delta^{CDCl_3}_{TMS}$ (ppm): 2.43(3H, s), 3.92(3H, s), 6.10(1H, d, J=8.0Hz), 6.48(1H, s), 6.84(1H, d, J=8.0Hz), 7.44(1H, s), 7.60(1H, s), 7.78(1H, s) |
| 44 | C₂H₅— | 3-CH₃ | 5-H | 2-methylthienyl | 114.5~118 | $\delta^{CDCl_3}_{TMS}$ (ppm): 1.47(3H, t, J=8.0Hz), 2.48(3H, s), 4.12(2H, q, J=8.0Hz), 6.34(1H, d, J=8.0Hz), 6.92(1H, d, J=8.0Hz), 7.18(1H, d, J=4.0Hz), 7.30-7.55(2H, m), 7.88(1H, s) |
| 45 | (CH₃)₂CH— | 3-CH₃ | 5-H | 2-methylthienyl | 143~144 | $\delta^{CDCl_3}_{TMS}$ (ppm): 1.46(6H, d, J=7.0Hz), 2.46(3H, s), 4.40(1H, m, J=7.0Hz), 6.12(1H, d, J=8.0Hz), 6.94(1H, d, J=8.0Hz), 7.18(1H, d, J=4.0Hz), 7.3-7.5(2H, m), 7.89(1H, s) |
| 46 | CH₃— | 3-CH₂OCH₃ | 5-H | 2-methylfuryl | Oil | $\delta^{CDCl_3}_{TMS}$ (ppm): 3.44(3H, s), 3.94(3H, s), 4.76(2H, s), 6.29(1H, d, J=8.0Hz), 6.42(1H, dd, J=3.0 & 1.0Hz), 6.58(1H, d, J=3.0Hz), 7.49(1H, d, J=1.0Hz), 7.70(1H, d, J=8.0Hz), 7.85(1H, s) |

TABLE 1-continued $$\text{(I)}$$

Structure: pyrazole with R², R³ substituents, N-R¹, and -CONHCH(CN)R⁴ group

| Compound No. | R¹ (in general formula (I)) | R² | R³ | R⁴ | Physical property (m.p. °C.) | NMR (100MHz) |
|---|---|---|---|---|---|---|
| 47 | CH₃— | 3-H | 5-OCH₃ | 2-furyl (O ring) | 148~149.5 | $\delta_{TMS}^{CDCl_3}$ (ppm): 3.78(3H, s), 4.40(3H, s), 6.35(1H, d, J=7.0Hz), 6.42(1H, dd, J=3.0 & 1.0Hz), 6.56(1H, d, J=3.0Hz), 7.25(1H, d, J=7.0Hz), 7.48(1H, d, J=1.0Hz), 7.79(1H, s) |
| 48 | C₂H₅— | 3-H | 5-CH₃ | 2-thienyl (S ring) | Oil | $\delta_{TMS}^{CDCl_3}$ (ppm): 1.38(3H, t, J=7.0Hz), 2.58(3H, s), 3.07(2H, q, J=7.0Hz), 6.45(1H, d, J=8.0Hz), 6.95-7.44(4H, m), 7.68(1H, s) |
| 49 | CH₃— | 3-CH₃ | 5-H | 5-methyl-2-furyl | 131~132 | $\delta_{TMS}^{CDCl_3}$ (ppm): 2.27(3H, s), 2.44(3H, s), 3.81(3H, s), 5.95(1H, d, J=3.0Hz), 6.22(1H, d, J=8.0Hz), 6.36(1H, d, J=3.0Hz), 7.02(1H, d, J=8.0Hz), 7.80(1H, s) |
| 50 | CH₃— | 3-OCH₃ | 5-H | 2-furyl | 141~143 | $\delta_{TMS}^{CDCl_3}$ (ppm): 3.70(3H, s), 3.91(3H, s), 6.17(1H, d, J=7.0Hz), 6.32(1H, dd, J=3.0 & 1.0Hz), 6.43(1H, d, J=3.0Hz), 7.39(1H, d, J=1.0Hz), 7.54(1H, d, J=7.0Hz), 7.74(1H, s) |
| 51 | CF₃CH₂— | 3-CH₃ | 5-H | 2-furyl | 149~150.0 | $\delta_{TMS}^{CDCl_3}$ (ppm): 2.64(3H, s), 4.78(2H, q, J=9.0Hz), 6.38(1H, d, J=8.0Hz), 6.42(1H, dd, J=3.0 & 1.0Hz), 6.58(1H,d,J=3.0Hz), 7.51(1H,d,J=1.0Hz), 8.15(1H,s),9.24(1H,d,J=8.0Hz) |
| 52 | CH₃— | 3-CH₃ | 4-H | —CH=C(CH₃)₂ | 92.5~94 | $\delta_{TMS}^{CDCl_3}$ (ppm): 1.82(6H,s), 2.25(3H,s), 4.12(3H,s), 5.34(1H,d,J=8.0Hz), 5.70(1H,t,J=8.0Hz), 6.40(1H,s), 6.80(1H,d,J=8.0Hz) |
| 53 | CH₃— | 3-CH₃ | 4-H | 2-thienyl | 111~112 | $\delta_{TMS}^{CDCl_3}$ (ppm): 2.21(3H, s), 4.09(3H, s), 6.40(1H, s), 6.41(1H, d, J=8.0Hz), 6.85-7.44(4H, m) |
| 54 | CH₃— | 3-CH₃ | 4-H | 5-methyl-2-thienyl | 107.5~109 | $\delta_{TMS}^{CDCl_3}$ (ppm): 2.23(3H, s), 4.08(3H, s), 6.23(1H, d, J=8.0Hz), 6.36(1H, s), 6.95(1H, d, J=8.0Hz), 7.08-7.55(3H, m) |

TABLE 1-continued $$R^2 \underset{N\underset{\underset{R^1}{N}}{}}{\overset{R^3}{\rule{0pt}{0pt}}} -CONHCH\overset{CN}{\underset{R^4}{}} \quad (I)$$

| Compound No. | In general formula (I) | | | | Physical property (m.p. °C.) | NMR (100MHz) |
|---|---|---|---|---|---|---|
| | $R^1$ | $R^2$ | $R^3$ | $R^4$ | | |
| 55 | CH$_3$— | 3-CH$_3$ | 4-H | (2-furyl) | 105~106 | $\delta^{CDCl_3}_{TMS}$ (ppm): 2.21(3H, s), 4.10(3H, s), 6.31(1H, d, J=8.0Hz), 6.32–6.44(2H, m), 6.44(1H, s), 7.40(1H, d, J=8.0Hz), 7.46(1H, br s) |
| 56 | CH$_3$— | 3-CH$_3$ | 4-H | —CH$_2$CH$_2$CH$_3$ | Oil | $\delta^{CDCl_3}_{TMS}$ (ppm): 1.0(3H, t, J=7.0Hz), 1.44–2.02(4H, m), 2.24(3H, s), 4.11(3H, s), 5.04(1H, q, J=8.0Hz), 6.45(1H, s), 7.37(1H, d, J=8.0Hz) |
| 57 | CH$_3$— | 3-CH$_3$ | 4-H | (phenyl) | 135~136 | $\delta^{CDCl_3}_{TMS}$ (ppm): 2.18(3H, s), 4.01(3H, s), 6.36(1H, d, J=8.0Hz), 6.77(1H, s), 7.36–7.68(5H, m), 9.63(1H, d, J=8.0Hz) |

The following Synthesis Examples specifically illustrate the process for producing the compounds of this invention.

SYNTHESIS EXAMPLE 1

Synthesis of alpha-(1,3-dimethylpyrazol-4-yl-carbonylamino)-(2-furyl)acetonitrile (compound No. 33):

Ammonium chloride (8.3 g) and 5.0 g of sodium cyanide were dissolved in 50 ml of water, and 15 ml of diethyl ether, 8.0 ml of 28% aqueous ammonia and 1.0 g of triethylbenzyl ammonium bromide were added to the solution. The mixture was cooled to 5° C. over an ice bath. With stirring, 8.0 g of 2-furylaldehyde was added dropwise, and the mixture was stirred at the above temperature for 25 hours. After the reaction, the ether layer was separated, and the aqueous layer was extracted three times with diethyl ether. The ether layers were combined, dried over anhydrous sodium sulfate, and concentrated under reduced pressure. The residue was mixed with 100 ml of ethyl acetate and cooled to 0° to 5° C. Then, 4.2 g of triethylamine was added, and with stirring, 3.9 g of 1,3-dimethylpyrazole-4-carboxylic acid chloride was gradually added. After the addition, the mixture was stirred further at room temperature for 2 hours. Water (50 ml) was added, and the precipitated triethylamine hydrochloride was dissolved in it. The ethyl acetate layer was separated, washed with water, dried over anhydrous sodium sulfate, and distilled under reduced pressure to remove the solvent. The residue was chromatographed on a silica gel column. The column was eluted with hexane/ethyl acetate to give 3.9 g (yield 65.0%) of the desired alpha-(1,3-dimethylpyrazol-4-ylcarbonylamino)-(2-furyl-)acetonitrile.

Melting point: 121.5°–122.5° C.

SYNTHESIS EXAMPLE 2

Synthesis of alpha-(1-isopropyl-3-methylpyrazol-4-ylcarbonylamino)-(2-thienyl)acetonitrile (compound No. 32):

Ammonium chloride (6.7 g) and 4.0 g of sodium cyanide were dissolved in 50 ml of water, and 15 ml of diethyl ether, 7.0 ml of 28% ammonia and 1.0 g of triethylbenzyl ammonium chloride were added to the solution. The mixture was cooled to 5° C. over an ice bath, and with stirring, 7.5 g of 2-thiophenaldehyde was added dropwise. The mixture was stirred further at the above temperature for 20 hours. After the reaction, the ether layer was separated, and the aqueous layer was extracted three times with diethyl ether. The ether layers were combined, dried over anhydrous sodium sulfate, and concentrated under reduced pressure. The residue was mixed with 50 ml of tetrahydrofuran, and cooled to 0° to 5° C. Then, 3.4 g of triethylamine was added, and 4.1 g of 1-isopropyl-3-methylpyrazole-4-carboxylic acid chloride was gradually added. After the addition, the mixture was further stirred at room temperature for 3 hours. The precipitated triethylamine hydrochloride was separated by filtration, and the filtrate was distilled under reduced pressure to remove the solvent. The residue was chromatographed on a silica gel column. The column was eluted with hexane/ethyl acetate to give 3.2 g (yield 50.4%) of the desired alpha-(1-isopropyl-3-methylpyrazol-4-ylcarbonylamino)-(2-thienyl)-acetonitrile.

Melting point: 140.5°–141.5° C.

SYNTHESIS EXAMPLE 3

Synthesis of alpha-(1,3-dimethylpyrazol-4-yl-carbonylamino)-(3-thienyl)acetonitrile (compound No. 38):

Ammonium chloride (10.0 g) and 6.0 g of sodium cyanide were dissolved in 50 ml of water, and 15 ml of diethyl ether, 9.5 ml of 28% aqueous ammonia and 1.0 g of triethylbenzyl ammonium chloride were added to the solution. The mixture was cooled to 5° C. over an ice bath, and with stirring, 11.2 g of 3-thiophenyaldehyde was added dropwise. The mixture was stirred further at the above temperature for 24 hours. After the reaction, the ether layer was separate, and the aqueous layer was extracted three times with diethyl ether. The ether layers were combined, dried over anhydrous sodium sulfate, and concentrated under reduced pressure. The residue was mixed with 100 ml of diethyl ether, and cooled to 0° to 5° C. Then, 4.2 g of triethylamine was added, and with stirring, 3.9 g of 1,3-dimethylpyrazole-4-carboxylic acid chloride was gradually added. After the addition, the mixture was stirred further at the above temperature for 1 hour. The precipitated triethylamine hydrochloride was separated by filtration, and the filtrate was distilled under reduced pressureto remove the solvent. The residue was chromatographed on a silica gel column. The column was eluted with benzene/ethyl acetate to give 4.8 g (yield 75.0%) of alpha-(1,3-dimethylpyrazol-4-yl-carbonylamino)-(3-thienyl)-acetonitrile).

Melting point: 113.0°–114.5° C.

SYNTHESIS EXAMPLE 4

Synthesis of alpha-(1-methyl-3-methoxymethylpyrazol-4-ylcarbonylamino)-(2-furyl)acetonitrile (compound No. 46):

In 100 ml of ethyl acetate was suspended 3.2 g of alpha-(2-furyl)-aminoacetonitrile hydrochloride, and with ice cooling, 4.5 g of triethylamine was added. Then, 3.8 g of 1-methyl-3-methoxymethylpyrazole-4-carboxylic acid chloride was gradually added at 0° to 5° C. with stirring. After the addition, the mixture was further stirred at room temperature for 2 hours. Water (50 ml) was added to dissolve the precipitated triethylamine hydrochloride. The ethyl acetate layer was separated, washed with water, dried over anhydrous sodium sulfate, and distilled under reduced pressure to remove the solvent. The residue was chromatographed on a silica gel column, and the column was eluted with hexane/ethyl acetate to give 4.3 g (yield 78.6%) of the desired alpha-(1-methyl-3-methoxymethylpyrazol-4-ylcarbonylamino)-(2-furyl)acetonitrile.

SYNTHESIS EXAMPLE 5

Synthesis of alpha-(1,3-dimethylpyrazol-4-yl-carbonylamino)-(2-pyrrolyl)acetonitrile (compound No. 42):

Ammonium chloride (8.3 g) and 5.0 g of sodium cyanide were dissolved in 50 ml of water, and 15 ml of diethyl ether, 8.0 ml of 28% aqueous ammonia and 1.0 g of triethyl benzyl ammonium bromide were added. The mixture was cooled to 5° C. over an ice bath, and with stirring, 8.0 g of pyrrole-2-carboxyaldehyde was added dropwise, and the mixture was stirred at the above temperature for 24 hours. After the reaction, the ether layer was separated, and the aqueous layer was extracted three times with diethyl ether. The ether layers were combined, dried over anhydrous sodium sulfate, and concentrated under reduced pressure. The residue was mixed with 100 ml of ethyl acetate, and cooled to 0° to 5° C. Then, 4.2 g of triethylamine was added, and with stirring, 3.9 g of 1,3-dimethylpyrazole-4-carboxylic acid chloride was gradually added. After the addition, the mixture was further stirred at room temperature for 2 hours. Water (50 ml) was added to dissolve the precipitated triethylamine hydrochloride. The ethyl acetate layer was separated, washed with water, dried over anhydrous sodium acetate, and distilled under reduced pressure to remove the solvent. The residue was chromatographed on a silica gel column, and the column was eluted with hexane/ethyl acetate to give 4.4 g (yield 73.1%) of the desired alpha-(1,3-dimethylpyrazol-4-ylcarbonylamino)-(2-pyrrolyl)acetonitrile.

Melting point: 174°–176° C.

SYNTHESIS EXAMPLE 6

Synthesis of 2-(1,3-dimethylpyrazol-4-ylcarbonylamino)-4-methyl-3-pentenenitrile (compound No. 1):

Ammonium chloride (8.3 g) and 5.0 g of sodium cyanide were dissolved in 50 ml of water, and 15 ml of diethyl ether and 8 ml of 28% aqueous ammonia were added to the solution. The mixture was cooled to 5° C. over an ice bath, and with stirring, 7.0 g of 3-methyl-2-butenal was added. The mixture was further stirred at the above temperature for 24 hours. After the reaction, the ether layer was separated, and the aqueous layer was extracted three times with diethyl ether. The ether layers were combined, dried over anhydrous sodium sulfate, and concentrated under reduced pressure. The residue was mixed with 100 ml of diethyl ether, and cooled to 0° to 5° C. Then, 4.2 g of triethylamine was added, and with stirring, 3.9 g of 1,3-dimethylpyrazole-4-carboxylic acid ch chloride was gradually added. After the addition, the mixture was further stirred at the above temperature for 1 hour. The precipitated triethylamine hydrochloride was separated by filtration, and the filtrate was distilled under reduced pressure to remove the solvent. The residue was chromatographed on a silica gel column, and the column was eluted with benzene/ethyl acetate to give 3.7 g (yield 64.6%) of the desired 2-(1,3-dimethylpyrazol-4-yl-carbonylamino)-4-methyl-3-pentenenitrile.

Melting Point: 110.5°–111.5° C.

SYNTHESIS EXAMPLE 7

Synthesis of 2-(1,3-dimethylpyrazol-4-ylcarbonylamino)-4-chloro-3-pentenenitrile (compound No. 4):

Ammonium chloride (6.7 g) and 4.0 g of sodium cyanide were dissolved in 50 ml of water, and 15 ml of diethyl ether and 7 ml of 28% aqueous ammonia were added to the solution. The mixture was cooled to 5° C. over an ice bath, and with stirring, 7.0 g of 3-chloro-2-butenal was added. The mixture was further stirred at the above temperature for 12 hours. After the reaction, the ether layer was separated, and the aqueous layer was extracted with diethyl ether three times. The ether layers were combined, dried over anhydrous sodium sulfate, and concentrated under reduced pressure. The residue was mixed with 50 ml of tetrahydrofuran and cooled to 0° to 5° C. Then, 3.4 g of triethylamine was added, and with stirring, 3.1 g of 1,3-dimethylpyrazole-4-carboxylic acid chloride was gradually added. After the addition, the mixture was further stirred at the above temperature for 1 hour. The precipitated triethylamine hydrochloride was separated by filtration, and the filtrate was distilled under reduced pressure to remove the solvent. The residue was chromatographed on a silica gel column, and the column was eluted with hexane/ethyl acetate to give 2.6 g (yield 52.5%) of the desired 2-(1,3-dimethylpyrazol-4-ylcarbonylamino)-4-chloro-3-pentenenitrile.

Melting point 113°–114 °C.

SYNTHESIS EXAMPLE 8

Synthesis of 2-(1-allyl-3-methylpyrazol-4-yl-carbonylamino)-4-methyl-3-pentenenitrile (compound No. 14):

Ammonium chloride (8.3 g) and 5.0 g of sodium cyanide were dissolved in 50 ml of water, and 15 ml of diethyl ether and 8.0 ml of 28% aqueous ammonium were added to the solution. The mixture was cooled with ice to 5° C., and with stirring, 7.0 g of 3-methyl-2-butenal was added dropwise. The mixture was stirred further at the above temperature for 24 hours. After the reaction, the ether layer was separated, and the aqueous layer was extracted with diethyl ether three times. The ether layers were combined, dried over anhydrous sodium sulfate, and concentrated under reduced pressure. The residue was mixed with 100 ml of diethyl ether, and cooled to 0° to 5° C. Then, 4.2 g of triethylamine was added. Furthermore, crude 1-allyl-3-methylpyrazole-4carboxylic acid synthesized by method B in Referential Synthesis Examples given hereinafter was converted to 1-allyl-3-methylpyrazole-4-carboxylic acid chloride in a customary manner. The crude product (4.5 g) was gradually added with stirrig. After the addition, the mixture was further stirred at the above temperature for 1 hour. The precipitated triethylamine hydrochloride was separated by filtration, and the filtrate was distilled under reduced pressure to remove the solvent. The residue was chromatographed on a silica gel column, and the column was eluted with hexane/ethyl acetate to give 4.3 g (yield 67.9%) of the desired 2-(1-allyl-3-methylpyrazole-4-ylcarbonylamino)-4-methyl-3-pentenenitrile.

SYNTHESIS EXAMPLE 9

Synthesis of 2-(1,3-dimethylpyrazol-5-ylcarbonylamino)-4-methyl-3-pentenenitrile (compound No. 52):

Ammonium chloride (8.3 g) and 5.0 g of sodium cyanide were dissolved in 50 ml of water, and 15 ml of diethyl ether and 8.0 ml of 28% aqueous ammonia were added. The mixture was cooled to 5° C. over an ice bath, and with stirring, 7.0 g of 3-methyl-2-butenal was added dropwise. The mixture was stirred further at the above temperature for 24 hours. After the reaction, the ether layer was separated, and the aqueous layer was extracted with diethyl ether three times. The ether layers were combined, dried over anhydrous sodium sulfate, and concentrated under reduced pressure. The residue was mixed with 100 ml of diethyl ether, and cooled to 0° to 5° C. Then, 4.2 g of triethylamine was added, and with stirring, 3.9 g of 1,3-dimethylpyrazol-5-carboxylic acid chloride was added gradually. After the addition, the mixture was stirred further at the above temperature for 1 hour. The precipitated triethylamine hydrochloride was separated by filtration, and the filtrate was distilled under reduced pressure to remove the solvent. The residue was chromatographed on a silica gel column, and the column was eluted with benzene/ethyl acetate to give 3.7 g (yield 64.6%) of the desired 2-(1,3-dimethylpyrazol-5-ylcarbonylamino)-4-methyl-3-pentenenitrile.

Melting point: 92.5°–94.0° C.

SYNTHESIS EXAMPLE 10

Synthesis of 2-(1,3-dimethylpyrazol-5-ylcarbonylamino)pentanenitrile (compound No. 56):

A mixture of 3.6 g of n-butylaldehyde and 10 ml of methanol was added dropwise with stirring to a mixture of 7.9 g of ammonium chloride, 6.6 g of sodium cyanide, 47 ml of 28% aqueous ammonia and 23 ml of methanol at 25 to 30° C., and the mixture was further stirred at the above temperature for 5 hours. After the reaction, the reaction mixture was discharged into 100 ml of water and extracted with diethyl ether three times. The ether layers were combined, dried over anhydrous sodium sulfate and concentrated under reduced pressure. The residue was mixed with 100 ml of diethyl ether, and cooled to 0° to 5° C. Then, 4.2 g of triethylamine was added, and with stirring, 3.9 g of 1,3-dimethylpyrazole-5-carboxylic acid chloride was gradually added. After the addition, the mixture was stirred further at the above temperature for 1 hour. The precipitated triethylamine hydrochloride was separated by filtration, and the filtrate was distilled under reduced pressure to remove the solvent. The residue was chromatographed on a silica gel column, and the column was eluted with hexane/ethyl acetate to give 4.1 g (yield 75.6%) of the desired 2-(1,3-dimethylpyrazol-5-ylcarbonylamino)pentanenitrile as an oil.

SYNTHESIS EXAMPLE 11

Synthesis of alpha-(1,3-dimethylpyrazol-5-yl-carbonylamino)-phenylacetonitrile (compound No. 57):

Mandelonitrile (1.6 g) was dissolved in 30 ml of methanol, and with stirring, ammonia gas was blown into the solution until the starting mandelonitrile disappeared. The reaction product was concentrated under reduced pressure, and 50 ml of diethyl ether and then 2.5 g of triethylamine were added to the residue. The mixture was cooled to 5° C. over an ice bath, and with stirring, 1.6 g of 1,3-dimethylpyrazole-5-carboxylic acid chloride was gradually added. After the addition, the mixture was further stirred at the above temperature for 1 hour. The precipitated triethylamine hydrochloride was separated by filtration, and the filtrate was distilled under reduced pressure to remove the solvent. The residue was chromatographed on a silica gel column, and the column was eluted with hexane/ethyl acetate to give 1.7 g (yield 67.0%) of the desired alpha-(1,3-dimethylpyrazol-5-ylcarbonylamino)-phenylacetonitrile.

Melting point: 135°–136° C.

The following Referential Examples specifically illustrate the process for producing the starting pyrazolecarboxylic esters and pyrazolecarboxylic acids. When separation of isomers from the intermediate was difficult, the crude product was directly submitted to the next step, and purified in the final step.

REFERRENTIAL EXAMPLE 1

Synthesis of 1,3-dimethylpyrazole-4-carboxylic acid (compound No. I-1; by method A):

A mixture of 18.6 g (0.1 mole) of ethyl 2-ethoxymethyleneacetoacetate and 47 ml of ethanol was cooled to 5° C. over an ice bath, and with stirring, 6.9 g (0.15 mole) of methylhydrazine was added dropwise. After the addition, the mixture was stirred under reflux for 4 to 5 hours. After the reaction, the reaction mixture was cooled to room temperature, and 230 ml of water was added. After salting out, the reaction mixture was extracted three times with ethyl acetate. The ethyl acetate layers were combined, washed with a saturated aqueous solution of sodium chloride, dried over sodium sulfate, and concentrated under reduced pressure to give 16.7 g of a crude ester. At room temperature, 16.7 g of the crude ester was added to a mixture of 16.7 g of sodium hydroxide and 33 ml of water with stirring. The mixture was stirred at 100° to 110° C. for 3 to 4 hours. After the reaction, the reaction mixture was cooled to room temperature, and 42 ml of water was added. While cooling the reaction solution, concentrated hydrochloric acid was added to adjust its pH to 4 to 5. The precipitated crystals were collected by filtration, dried, and recrystallized from water to give 9.8 g (yield 70%) of the desired 1,3-dimethylpyrazole-4-carboxylic acid.

Melting point: 190°–190.5° C.

REFERENTIAL EXAMPLE 2

Synthesis of 1-methyl-5-methoxypyrazole-4carboxylic acid [by method (B)]:

3.4 g of ethyl 5-hydroxy-1-methylpyrazole-4-caroxylate (Japanese Laid-Open Patent Publication No. 122488/1984) obtained from ethyl ethoxymethylenemalonate and methylhydrazine was dissolved in 80 ml of tetrahydrofuran, and converted into a salt using 0.8 g of sodium hydride. Methyl iodide (2.8 g) was added, and the mixture was stirred at 40° C. for 3 hours. After the reaction, the mixture was filtered, and the filtrate was concentrated to give 1.7 g (yield 46%) of 1-methyl-5-methoxypyrazole-4-carboxylate.

Ethyl 1-methyl-5-methoxypyrazole-4-carboxylate (1.4 g) was stirred at room temperature for 2 hours together with 30 ml of ethanol, 10 ml of water and 2 g of potassium hydroxide. Ethanol was removed from the reaction solution under reduced pressure. From the aqueous layer, 1.29 g (yield 99%) of the desired 1-methyl-5-methoxypyrazole-4-carboxylic acid was obtained by acid precipitation.

Melting point: 225° C. (decomp.)

REFERENTIAL EXAMPLE 3

Synthesis of 1-(gamma-chloroallyl)-3-methylpyrazole-4-carboxylic acids (compounds Nos. I-10 and I-11; by method C):

Ethyl 3-methylpyrazole-4-carboxylate (5.0 g) was added to sodium alcoholate prepared from 0.75 g of metallic sodium and 30 ml of ethanol. To the homogeneous mixture was added 3.6 g of 1,3-dichloropropene, and the mixture was refluxed for 2 hours. After the reaction, the reaction mixture was discharged into water and extracted with ethyl acetate. The extract was chromatographed on a silica gel column, and the column was eluted with hexane/ethyl acetate to give 2.5 g (34%) of a Z isomer of ethyl 1-(gamma-chloroallyl)-3-methylpyrazole-4-carboxylate and 1.5 g (20 %) of its E isomer. The Z isomer (2.5 g) was stirred under heat for 4 hours together with a mixture of 25 ml of ethanol, 2.5 g of sodium hydroxide and 25 ml of water. After the reaction, the reaction mixture was cooled to room temperature, and with cooling, concentrated hydrochloric acid was added to adjust its pH to 4 to 5. The precipitated crystals were collected by filtration and dried. Recrystallization from water gave 0.3 g (yield 14%) of the Z isomer of 1-(gamma-chloroallyl)-3-methylpyrazole-4-carboxylic acid. m.p. 96°–100° C.

By the same operation, its E isomer was obtained in an amount of 0.34 g (yield 30%). m.p. 152°–156° C.

REFERENTIAL EXAMPLE 4

Synthesis of 1-methylpyrazole-4-carboxylic acid [compound No. I-5; by method (D)]:

3.9 g of 1-methylpyrazole-4-aldehyde (described in J. Chem. Soc., page 3314, 1957) was dissolved in 20 ml of acetone, and while heating the solution, the Jones reagent was added. After the reaction, the excess of the Jones reagent was treated with a dilute aqueous alkaline solution, and the precipitate was collected by filtration. The filtrate was made weakly acidic and extracted with ethyl acetate. The extract was dried over anhydrous sodium sulfate, and concentrated under reduced pressure to give 2.3 g (yield 52%) of 1-methylpyrazole-4-carboxylic acid. m.p. 205°–206° C.

REFERENTIAL EXAMPLE 5

Synthesis of ethyl 1,3-dimethylpyrazole-5-carboxylate [by method (E)]:

Methylhydrazine (10 g) was added dropwise with stirring and ice cooling to a mixture of 30 g of acetopyruvic acid and 120 ml of ethanol. With the generation of heat, the mixture changed from a colorless solution to a yellow solution. The solution was then stirred for 3 hours under reflux. Low-boiling materials were evaporated under reduced pressure to give 33.6 g of a yellow oil. The yellow oil was chromatographed on a silica gel column (eluent: benzene/ethyl acetate=1/1) to give 8.6 g (yield 27%) of ethyl 1,3-dimethylpyrazole-5-carboxylate as a yellow oil.

NMR (CDCl$_3$)$\delta$: 1.46 (3H, t, J=7.0 Hz), 2.38 (3H, s), 4.18 (3H, s), 4.47 (2H, q, J=7.0 Hz), 6.65 (1H, s).

Ethyl 1,5-dimethylpyrazole-3-carboxylic acid as an isomer was obtained in an amount of 22.0 g (yield 69%) as a colorless oil.

NMR (CDCl$_3$)$\delta$: 1.38 (3H, t, J=7.0 Hz), 2.31 (3H, s), 3.82 (3H, s), 4.32 (2H, q, J=7.0 Hz), 6.26 (1H, s).

By the same method as above, other pyrazolecarboxylic acids used in this invention were synthesized. The compounds and the properties of thereof are shown in Table 2.

The resulting pyrazolecarboxylic acids were used after they were converted into acid chlorides of general formula (III) in a customary manner.

The desired compounds of general formula (I) can be obtained by converting the pyrazolecarboxyic acids into acid chlorides in a customary manner without recrystallization, and reacting them with the aminoacetonitriles of general formula (IV), and purifying the crude products by column chromatography.

Other compounds in accordance with this invention can be synthesized substantially in accordance with the procedures of Synthesis Examples 1 to 11.

TABLE 2

$$R^2 \underset{N}{\overset{R^3}{\underset{\underset{R^1}{N}}{\diagdown}}} CO_2H$$

| Intermediate compound No. | R¹ (In the above general formula) | R² | R³ | Physical property (m.p. °C.) | Method of synthesis | NMR (100 MHz) |
|---|---|---|---|---|---|---|
| I-1 | $CH_3-$ | 3-$CH_3$ | 5-H | 190~190.5 | A | $\delta_{TMS}^{CDCl_3}$ (ppm): 2.49(3H,s), 3.88(3H,s), 7.86(1H,s), 10.64–11.24(1H,br s) |
| I-2 | $C_2H_5-$ | 3-$CH_3$ | 5-H | 158~159 | A | $\delta_{TMS}^{CDCl_3}$ (ppm): 1.52(3H,t,J=7.0Hz), 2.50(3H,s), 4.175(2H,q,J=7.0Hz), 7.92(1H,s), 10.52–10.80(1H,br s) |
| I-3 | $(CH_3)_2CH-$ | 3-$CH_3$ | 5-H | 162.5~164 | A | $\delta_{TMS}^{DMSO-d_6}$ (ppm): 1.42(6H,d,J=8.0Hz), 2.34(3H,s), 4.47(1H,m,J=8.0Hz), 8.13(1H,s), 10.6–11.4(1H,br s) |
| I-4 | 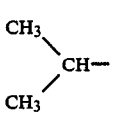 | 3-$CH_3$ | 5-H | 190~191 | D | $\delta_{TMS}^{DMSO-d_6}$ (ppm): 2.52(3H,s), 7.30–7.55(3H,m), 7.8–7.9(2H,m), 8.82(1H,s), 12.3(1H,br) |
| I-5 | $CH_3-$ | 3-H | 5-H | 205~206 | D | $\delta_{TMS}^{DMSO-d_6}$ (ppm): 3.89(3H,s), 7.84(1H,s), 7.92(1H,s), 11–12(1H,br) |
| I-6 | $CH_3-$ | 3-$CH_3$ | 5-Cl | 194~196.5 | D | $\delta_{TMS}^{DMSO-d_6}$ (ppm): 2.36(3H,s), 3.77(3H,s), 11–13(1H,br) |
| I-7 | $CH_3-$ | 3-H | 5- | 210 (decomp.) | A | $\delta_{TMS}^{DMSO-d_6}$ (ppm): 3.92(3H,s), 7.3–7.5(3H,s), 7.7–7.9(2H,m), 8.29(1H,s), 11–12(1H,br) |
| I-8 | $CH_3-$ | 3-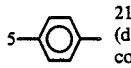 | 5-H | 215~218 | A | $\delta_{TMS}^{DMSO}-d_6$ (ppm): 3.65(3H,s), 7.48(5H,s), 7.87(1H,s), 11–12(1H,br) |
| I-9 | $CH_3CH_2CH_2CH_2-$ | 3-H | 5-H | 103~106 | D | $\delta_{TMS}^{DMSO-d_6}$ (ppm): 0.90(3H,t,J=6.0Hz), 1.1–1.4(2H,m), 1.6–1.9(2H,m), 4.16(2H,t,J=6.0Hz), 7.81(1H,s), 8.25(1H,s), 11.9–12.5(1H,br) |
| I-10 |  (Z) | 3-$CH_3$ | 5-H | 96~100 | C | $\delta_{TMS}^{DMSO-d_6}$ (ppm): 2.32(3H,s), 4.72(2H,d,J=7.0Hz), 6.14(1H,dt,J=17.0 & 7.0Hz), 6.56(1H,d,J=17.0Hz), 8.10(1H,s), 10–11(1H,br) |
| I-11 | 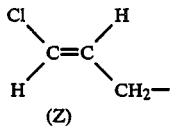 (E) | 3-$CH_3$ | 5-H | 152~156 | C | $\delta_{TMS}^{DMSO-d_6}$ (ppm): 2.32(3H,s), 4.87(2H,dd,J=7.0 & 1.0Hz), 6.15(1H,dt,J=10.0 & 7.0Hz), 6.53(1H,dd,J=10.0 & 1.0Hz), 8.12(1H,s), 10–11(1H,br) |
| I-12 | $CH_3(CH_2)_2CH_2-$ | 3-$CH_3$ | 5-H | 73~75 | A | $\delta_{TMS}^{CDCl_3}$ (ppm): 0.96(3H,t,J=8.0Hz), 1.2–1.6(2H,m), 1.7–2.0(2H,m), 2.50(3H,s), 4.10(2H,t,J=8.0Hz), 7.88(1H,s), 11.36(1H,s) |
| I-13 | $(CH_3)_3C-$ | 3-$CH_3$ | 5-H | 133~135 | A | $\delta_{TMS}^{DMSO-d_6}$ (ppm): 1.62(9H,s), 2.70(3H,s), 7.60(1H,s), 11.40(1H,br) |
| I-14 | $CH_3(CH_2)_6CH_2-$ | 3-$CH_3$ | 5-H | 42~44 | A | $\delta_{TMS}^{CDCl_3}$ (ppm): 0.88(3H,t,J=8.0Hz), 1.1–1.5(10H,m), 1.6–2.0(2H,m), 2.48(3H,s), 4.04(2H,t,J=8.0Hz), 7.84(1H,s), 11.44(1H,s) |
| I-15 | $CH_3-$ | 3-$C_2H_5$ | 5-H | 149~151 | A | $\delta_{TMS}^{DMSO-d_6}$ (ppm): 1.16(3H,t,J=8.0Hz), 2.74(2H,q,J=8.0Hz), 3.76(3H,s), |

TABLE 2-continued $$\text{R}^2\underset{N}{\overset{R^3}{\underset{|}{\underset{R^1}{\bigvee}}}}\text{CO}_2\text{H}$$

| Intermediate compound No. | In the above general formula R¹ | R² | R³ | Physical property (m.p. °C.) | Method of synthesis | NMR (100 MHz) |
|---|---|---|---|---|---|---|
| I-16 | $C_2H_5-$ | 3-$C_2H_5$ | 5-H | Oil | A | $\delta_{TMS}^{CDCl_3}$ (ppm): 1.28(3H,t,J=8.0Hz), 1.52(3H,t,J=8.0Hz), 2.96(2H,q,J=8.0Hz), 4.18(2H,q,J=8.0Hz), 7.96(1H,s), 11.75(1H,br) |
| I-17 | $CH_3(CH_2)_2CH-$ | 3-$C_2H_5$ | 5-H | Oil | A | $\delta_{TMS}^{CDCl_3}$ (ppm): 0.96(3H,t,J=8.0Hz), 1.2–1.5(5H,m), 1.7–2.0(2H,m), 2.94(2H,q,J=8.0Hz), 4.10(2H,t,J=8.0Hz), 7.90(1H,s), 11.34(1H,s) 7.96(1H,s), 11.94(1H,s) |
| I-18 | $CH_3-$ | 3-$CH_2CH_2CH_3$ | 5-H | 141~142 | A | $\delta_{TMS}^{DMSO-d_6}$ (ppm): 0.94(3H,t,J=8.0Hz), 1.4–1.8(2H,m,J=8.0Hz), 2.76(2H,t,J=8.0Hz), 3.80(3H,s), 8.08(1H,s), 11.9(1H,br) |
| I-19 | $CH_3-$ | 3-$CH(CH_3)_2$ | 5-H | 160~163 | A | $\delta_{TMS}^{DMSO-d_6}$ (ppm): 1.22(6H,d,J=6.0Hz), 3.3–3.7(1H,m,J=6.0Hz), 3.80(3H,s), 8.06(1H,s), 12.00(1H,br) |
| I-20 | $CH_3$ | 3-$CF_3$ | 5-H | 188~190 | A | $\delta_{TMS}^{DMSO-d_6}$ (ppm): 3.96(3H,s), 8.44(1H,s), 12.70(1H,br) |
| I-21 | $CH_3-$ | 3-$CH_2OCH_3$ | 5-H | 125~132 | A | $\delta_{TMS}^{DMSO-d_6}$ (ppm): 3.29(3H,s), 3.84(3H,s), 4.78(2H,s), 7.73(1H,s), 10.5–11.5(1H,br) |
| I-22 | $CF_3CH_2-$ | 3-$CH_3$ | 5-H | 136~138 | A | $\delta_{TMS}^{DMSO-d_6}$ (ppm): 2.55(3H,s), 5.12(2H,q, J=9.0Hz), 7.87(1H,s), 12.6(1H,br) |
| I-23 | $CH_3-$ | 3-$OCH_3$ | 5-H | 225 (decomp.) | B | $\delta_{TMS}^{DMSO-d_6}$ (ppm): 3.66(3H,s), 3.78(3H,s), 7.96(1H,s), 11.3–11.9(1H,br) |

The production of the agricultural and horticultural fungicide of this invention will be illustrated by the following Formulation Examples.

FORMULATION EXAMPLE 1

Dust:

Three parts of compound No. 1, 20 parts of diatomaceous earth, 30 parts of terra alba, and 47 parts of talc were uniformly pulverized and mixed to obtain 100 parts of a dust.

FORMULATION EXAMPLE 2

Wettable powder:

Thirty parts of compound No. 2, 47 parts of diatomaceous earth, 20 parts of terra alba 1 part of sodium lignosulfonate and 2 parts of sodium alkylbenzenesulfonate were pulverized and mixed to obtain 100 parts of a wettable powder.

FORMULATION EXAMPLE 3

Emulsifiable concentrate:

Twenty parts of compound No. 3, 10 parts of cyclohexanone, 50 parts of xylene and 20 parts of Sorpol (surface-active agent made by Toho Chemical Co., Ltd.) were uniformly dissolved and mixed to obtain 100 parts of an emulsifiable concentrate.

FORMULATION EXAMPLE 4

Granules:

One part of compound No. 4, 78 parts of bentonite, 20 parts of talc and 1 part of sodium lignosulfonate were mixed, and kneaded with a suitable amount of water. The mixture was granulated by an extrusion granulator by an ordinary method and dried to obtain 100 parts of granules.

FORMULATION EXAMPLE 5

Granules:

Five parts of compound No. 3, 1 part of polyethylene glycol nonyl phenyl ether, 3 parts of polyvinyl alcohol and 91 parts of clay were uniformly mixed, and after addition of water, granulated, and dried to obtain 100 parts of granules.

FORMULATION EXAMPLE 6

Dust:

Two parts of compound No. 33, 40 parts of calcium carbonate and 58 parts of clay were uniformly mixed to obtain 100 parts of a dust.

FORMULATION EXAMPLE 7

Wettable powder:

Fifty parts of compound No. 5, 40 parts of talc, 5 parts of sodium laurylphosphate, and 5 parts of sodium alkylnaphthalenesulfonate were mixed to obtain 100 parts of a wettable powder.

FORMULATION EXAMPLE 8

Wettable powder:
Fifty parts of compound No. 1, 10 parts of sodium ligninsulfonate, 5 parts of sodium alkylnaphthalene, 10 parts of white carbon and 25 parts of diatomaceous earth were mixed and pulverized to obtain 100 parts of a wettable powder.

FORMULATION EXAMPLE 9

Flowable composition:
Forty parts of compound No. 30, 3 parts of carboxymethyl cellulose, 2 parts of sodium lignosulfonate, 1 part of sodium dioctylsulfosuccinate and 54 parts of water were wet-pulverized by a sand grinder to obtain 100 parts of a flowable composition.

The efficacy of the compounds of this invention as an agricultural and horticultural fungicide will be illustrated by the following Test Examples. In these Test Examples, the following compounds were used as controls.

A: alpha-(2,6-dichloropyridin-4-ylcarbonylamino)-(2-furyl)acetonitrile
B: alpha-(2-furylcarbonylamino)-(2-furyl)acetonitrile
C: 4-(2,4-dichlorobenzoyl)-5-benzoylmethoxy-1,3-dimethylpyrazole
D: alpha-benzoylaminopropioacetonitrile
E: zinc ethylenebis(dithiocarbamate) [zineb]
F: tetrachloroisophthalonitrile [TPN]

Control compounds A and B are described in Japanese Laid-Open Patent Publication No. 167978/1982 cited above. Compound C is a commercialy available paddy herbicide. Compound D is described in Justus Liebigs Ann. Chem., 1972, 764, pages 69–93, cited above. Compounds E and F are commercially available chemicals for controlling late blight of potato and downy mildew of cucumber.

TEST EXAMPLLE 1

Test for controlling potato late blight (preventive effect):

Potato (variety: "Danshaku", height about 25 cm) was grown in pots in a greenhouse. A test chemical was prepared by forming a wettable powder from each of the test compounds in accordance with the method of Formulation Example 8, and diluting it with water to a predetermined concentration. The chemical was sprayed by a spray gun (1.0 kg/cm$^2$) at a rate of 50 ml per three pots, and then air dried. A zoospore suspension was prepared from *Phytophthora infestans* cultured in advance for 7 days on a potato slice. The suspension was inoculated in the potato plants by spraying. The plants were maintained for 6 days at a temperature of 17° to 19° C. and a humidity of more than 95%, and then the degree of formation of lesions was examined.

The ratio of the area of lesions was observed and evaluated for each leaf, and the lesion index was determined. For each area, the lesion degree was calculated in accordance with the following equation.

$$\text{Lesion degree} = \frac{4n_4 + 2n_3 + 2n_2 + 1n_1 + 0n_0}{N}$$

The grading of evaluation was as follows.

| Lesion index | Ratio of the area of lesions |
|---|---|
| 0 | 0% |
| 1 | 1–5% |
| 2 | 6–25% |
| 3 | 26–50% |
| 4 | 51% or more |

$n_0$: the number of leaves having a lesion index of 0
$n_1$: the number of leaves having a lesion index of 1
$n_2$: the number of leaves having a lesion index of 2
$n_3$: the number of leaves having a lesion index of 3
$n_4$: the number of leaves having a lesion index of 4
$N = n_0 + n_1 + n_2 + n_3 + n_4$ The results are shown in Table 3.

TEST EXAMPLE 2

Test for controlling potato late blight (curative effect):

A zoospore suspension of *Phytophthora infestans* prepared as in Test Example 1 was inoculated in potato (variety: "Danshaku", height about 25 cm) grown in pots in a greenhouse by spraying. The plants were maintained for 20 hours at a temperature of 17° to 19° C. and a humidity of 95%. Then, a chemical in a predetermined concentration (obtained by preparing a wettable powder from each of the test compounds in accordance with Formulation Example 8, and diluting it to a predetermined concentration) was sprayed onto the plants by a spray gun (1.0 kg/cm$^2$) at a rate of 50 ml per three pots. After air-drying, the plants were again maintained for 6 days at a temperature of 17° to 19° C. and a humidity of more than 95%, and the degree of formation of lesions was examined.

The grading of evaluation and the lesion degree were the same as in Test Example 1. The results are shown in Table 3.

TEST EXAMPLE 3

Test for controlling cucumber downy mildew (preventive effect):

A chemical in a predetermined concentration (obtained by preparing a wettable powder of each of the test compounds in accordance with the method of Formulation Example 8, and diluting it with water to a predetermined concentration) was sprayed onto cucumber (variety: "Sagami Hanjiro"; in the stage where two main leaves developed) at a rate of 30 ml per three pots, and air dried. *Pseudoperonospora cubensis* was sampled from the lesions of cucumber leaves infected with downy mildew, and formed into a spore suspension by using deionized water. The suspension was inoculated in the cucumber plants in the pots by spraying. The pots were immediately maintained for 24 hours at a temperature of 18° to 20° C. and a humidity of more than 95%, and then transferred to a greenhouse (room temperature, 18° to 27° C.) Seven days later, the degree of formation of lesions was examined.

The grading of evaluation and the lesion degree were as in Test Example 1. The results are shown in Table 3.

TEST EXAMPLE 4

Test for controlling cucumber downy mildew (curative effect):

A zoospore suspension of *Pseudoperonospora cubensis* was prepared and sprayed onto the same cucumber plants as used in Test Example 3 to inoculate the fungus. The plants were maintained for 24 hours at a temperature of 18° to 20° C. and a humidity of more than 95%. A chemical in a predetermined concentration (obtained by preparing a wettable powder of each of the test compounds by the same method as in Formulation Example 8 and diluting it with water to a predetermined concentration) was sprayed onto the plants by means of a spray gun (1.0 kg/cm$^2$) at a rate of 30 ml per three pots). The pots were then transferred to a greenhouse (temperature 18° to 27° C.), and 7 days later, the degree of formation of lesions was examined.

The grading of evaluation and the lesion degree were the same as in Test Example 1. The results are shown in Table 3.

TEST EXAMPLE 5

Test on tomato late blight (soil drench):

A chemical (obtained by preparing a wettable powder of each of the test compounds in accordance with the method of Formulation Example 8 and diluting it with water to a predetermined concentration) was drenched at the roots of tomato (variety: "sekaiichi", height about 20 cm) grown in pots (diameter 7.5 cm) in a greenhouse at a rate of 2 ml per pot by using a pipette. The plants were maintained for 5 days in the greenhouse. A zoospore suspension of *Phytophthora infestans* cultivated in advance on a potato slice for 7 days. The suspension was sprayed onto the tomato plants treated with the chemical, and maintained at a temperature of 17° to 19° C. and a humidity of 95% or more for 6 days, and then the degree of formation of lesions was examined.

The grading of evaluation and the lesion degree were as shown in Test Example 1. The results are shown in Table 3.

In the foregoing Test Examples, the concentration of the active ingredient was 100 ppm in the case of spraying, and 15 g/are in the case of soil drench.

TABLE 3

| | Lesion Degree | | | | |
|---|---|---|---|---|---|
| | Potato late blight | | Cucumber downy mildew | | Tomato late blight |
| | Test Example 1 (preventive effect) | Test Example 2 (curative effect) | Test Example 3 (preventive effect) | Test Example 4 (curative effect) | Test Example 5 (soil drench) |
| Compound No. | | | | | |
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 0.3 | — | 0.1 | 0.4 | — |
| 7 | 0.4 | — | 0.1 | 0.3 | — |
| 8 | 0 | — | — | — | — |
| 9 | 0.5 | 0.8 | 0 | 0.1 | — |
| 13 | 0.1 | 0.6 | 0 | 0.5 | — |
| 14 | 0 | 0.1 | 0 | 0 | 0 |
| 18 | 0 | 0 | 0 | 0 | 0 |
| 19 | 0 | 0 | 0 | 0 | 0.1 |
| 20 | 0 | 0 | 0 | 0 | — |
| 24 | 0 | 0 | 0 | 0 | 0 |
| 25 | 0 | — | — | 0 | 0 |
| 26 | 0 | 0 | — | 0 | — |
| 28 | 0.1 | 0 | 0.2 | 0.3 | — |
| 30 | 0 | 0 | 0 | 0 | 0 |
| 31 | 0 | 0 | 0 | 0 | 0 |
| 32 | 0 | 0 | 0 | 0 | 0 |
| 33 | 0 | 0 | 0 | 0 | 0 |
| 34 | 0 | 0 | 0 | 0 | 0 |
| 35 | 0 | 0 | 0 | 0 | 0 |
| 36 | — | 0 | 0 | — | 0 |
| 37 | — | 0 | 0 | — | 0.2 |
| 38 | 0 | — | — | 0 | 0 |
| 42 | 0.5 | 1.4 | 0.4 | — | — |
| 43 | 0 | 0 | 0 | 0 | 0 |
| 44 | 0 | 0 | 0 | 0 | 0 |
| 45 | 0 | 0.4 | 0 | 0.3 | — |
| 46 | 0 | 0 | 0 | 0 | 0.6 |
| 52 | 0 | 0 | 0 | 0 | 0 |
| 54 | 0 | 0 | 0 | 0 | 0 |
| 55 | 0 | 0 | 0 | 0 | 0 |
| 56 | 0 | 0 | 0 | 0 | 0 |
| 57 | 0 | 0 | 0 | 0 | 0 |
| Control | | | | | |
| A | 2.4 | 2.6 | 2.0 | 2.1 | 3.0 |
| B | 2.0 | 2.4 | 2.7 | 2.1 | 3.0 |
| C | 3.7 | 3.8 | 3.8 | 3.9 | 3.0 |
| D | 3.5 | 3.2 | 3.5 | 3.3 | 4.0 |
| E | 2.5 | 3.2 | 2.4 | 3.5 | 4.0 |
| F | 2.3 | 3.6 | 2.1 | 3.6 | 4.0 |
| Non-treated | 3.8 | 3.4 | 4.0 | 3.5 | 4.0 |

The results given in Table 3 clearly demonstrate that the compounds of this invention show a high control effect against plant diseases induced by Phycomycetes such as potato late blight, tomato late blight and cucumber downy mildew not only by spraying but also by soil drench treatment. This is very contrastive to the fact that control compounds A, B, C and D considered to be fairly similar to the compounds of this invention show little or no controlling effects against these diseases. Furthermore, as compared with zinc ethylenebis(dithiocarbamate) and tetrachloroisophthalonitrile now marketed and widely used against these plant diseases, the compounds of the invention show a preventive effect at much lower dosages, and at the same time have a curative effect and a preventive effect by soil drench which are not possessed by these two commercial chemicals.

As is clearly seen from the above description, the pyrazole derivatives of this invention have an excellent control effect as an agricultural and horticultural fungicide against various plant diseases caused by Phycomycetes. Since they have a curative effect, they are expected to produce a control effect even when they are applied after the crops are infected.

The system of controlling diseases of agricultural and horticultural plants can be greatly altered by the compounds produced by this invention and this clearly will result in great savings of labor on the part of the growers. Accordingly, agricultural chemicals containing the pyrazole derivatives in accordance with this invention have excellent properties as agricultural and horticultural fungicides and are very useful.

What is claimed is:

1. A pyrazole derivative of general formula (I):

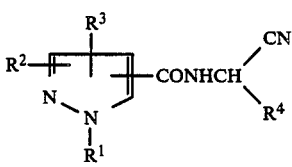
(I)

wherein $R^1$ is an alkyl group having 1 to 12 carbon atoms, a haloalkyl group having 1 to 6 carbon atoms, an alkenyl group having 2 to 6 carbon atoms, a haloalkenyl group having 2 to 6 carbon atoms or a phenyl group, $R^2$ and $R^3$ are each a hydrogen or halogen atom, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms or a phenyl group, and $R^4$ is an alkyl group having 1 to 6 carbon atoms, an alkenyl group having 2 to 6 carbon atoms, a haloalkenyl group having 2 to 6 carbon atoms, a phenyl group, or a heterocyclic aromatic group selected from the group consisting of a furyl group, a thienyl group, 2-pyrrole group and 3-pyrrole group which may be unsubstituted or substituted with a halogen atom or a lower alkyl group having 1 to 4 carbon atoms.

2. The pyrazole derivative of claim 1 wherein, in general formula (I), $R^1$ and $R^2$ are each an alkyl group having 1 to 6 carbon atoms, $R^3$ is a hydrogen atom, and $R^4$ is a member selected from the group consisting of a 2-furyl group, a 3-furyl group, a 2-thienyl group, a 3-thienyl group and a 2-pyrrole group which is unsubstituted or substituted with a methyl group or a halogen atom.

3. The pyrazole derivative of claim 2 wherein, in general formula (I), $R^4$ is a member selected from the group consisting of a 2-furyl group, a 3-furyl group, a 2-thienyl group and a 3-thienyl group.

4. The pyrazole derivative of claim 1 wherein, in general formula (I), $R^1$ and $R^2$ are each an alkyl group having 1 to 6 carbon atoms, $R^3$ is a hydrogen atom, and $R^4$ is a 2-methylpropen-1-yl group.

5. The pyrazole derivative of claim 1 which is represented by general formula (II):

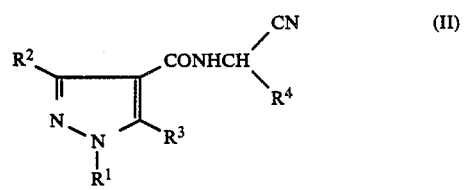
(II)

wherein $R^1$ and $R^2$ are each an alkyl group having 1 to 6 carbon atoms, $R^3$ is a hydrogen atom, and $R^4$ is a member selected from the group consisting of a 2-furyl group, a 3-furyl group, a 2-thienyl group and a 3-thienyl group.

6. The pyrazole derivative of claim 1 which is represented by general formula (II):

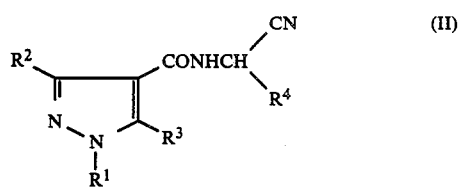
(II)

wherein $R^1$ and $R^2$ are each an alkyl group having 1 to 6 carbon atoms, $R^3$ is a hydrogen atom, an $R^4$ is a 2-methylpropen-1-yl group.

7. An agricultural and horticultural fungicidal composition comprising (a) a fungicidally effective amount of a pyrazole derivative of general formula (I):

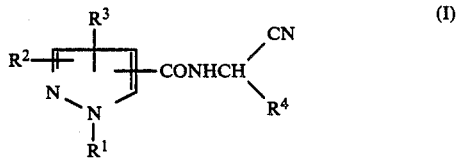
(I)

wherein $R^1$ is an alkyl group having 1 to 12 atoms, a haloalkyl group having 1 to 6 carbon atoms, an alkenyl group having 2 to 6 carbon atoms, a haloalkenyl group having 2 to 6 carbon atoms or a phenyl group, $R^2$ and $R^3$ are each a hydrogen or halogen atom, an alkyl group having 1 to 6 carbon atoms, a haloalkyl group having 1 to 6 carbon atoms, an alkoxy group having 1 to 6 carbon atoms, an alkoxyalkyl group having 2 to 6 carbon atoms or a phenyl group, and $R^4$ is an alkyl group having 1 to 6 carbon atoms, an alkenyl group having 2 to 6 carbon atoms, a haloalkenyl group having 2 to 6 carbon atoms, a phenyl group, or a heterocyclic aromatic group selected from the group consisting of a furyl group, a thienyl group, a 2-pyrrole group and a 3-pyrrole group which may be unsubstituted or substituted with a halogen atom or a lower alkyl group having 1 to 4 carbon atoms, as an active ingredient, and (b) a carrier and/or an adjuvant.

* * * * *